United States Patent
Blackburn

(10) Patent No.: US 12,018,009 B2
(45) Date of Patent: Jun. 25, 2024

(54) ALDH-2 INHIBITOR COMPOUNDS AND METHODS OF USE

(71) Applicant: Amygdala Neurosciences, Inc., San Francisco, CA (US)

(72) Inventor: Brent Blackburn, Los Altos, CA (US)

(73) Assignee: AMYGDALA NEUROSCIENCES, INC., San Francisco, CA (US)

( * ) Notice: Subject to any disclaimer, the term of this patent is extended or adjusted under 35 U.S.C. 154(b) by 0 days.

(21) Appl. No.: 18/209,165

(22) Filed: Jun. 13, 2023

(65) Prior Publication Data

US 2023/0399315 A1 Dec. 14, 2023

Related U.S. Application Data

(60) Provisional application No. 63/351,997, filed on Jun. 14, 2022.

(51) Int. Cl.

| | | |
|---|---|---|
| *C07D 401/04* | (2006.01) |
| *A61K 9/00* | (2006.01) |
| *A61K 9/20* | (2006.01) |
| *A61K 9/48* | (2006.01) |
| *A61K 47/06* | (2006.01) |
| *A61K 47/12* | (2006.01) |
| *A61K 47/14* | (2017.01) |
| *A61K 47/26* | (2006.01) |
| *A61K 47/36* | (2006.01) |
| *A61K 47/38* | (2006.01) |
| *A61K 47/44* | (2017.01) |
| *C07D 401/14* | (2006.01) |
| *C07D 403/04* | (2006.01) |

(52) U.S. Cl.
CPC .......... *C07D 401/04* (2013.01); *A61K 9/0014* (2013.01); *A61K 9/2009* (2013.01); *A61K 9/2013* (2013.01); *A61K 9/2027* (2013.01); *A61K 9/2054* (2013.01); *A61K 9/4825* (2013.01); *A61K 9/4858* (2013.01); *A61K 9/4866* (2013.01); *A61K 47/06* (2013.01); *A61K 47/12* (2013.01); *A61K 47/14* (2013.01); *A61K 47/26* (2013.01); *A61K 47/36* (2013.01); *A61K 47/38* (2013.01); *A61K 47/44* (2013.01); *C07D 401/14* (2013.01); *C07D 403/04* (2013.01)

(58) Field of Classification Search
CPC .................................................. C07D 401/04
See application file for complete search history.

(56) References Cited

U.S. PATENT DOCUMENTS

| | | | |
|---|---|---|---|
| 5,624,910 A | 4/1997 | Vallee |
| 6,121,010 A | 9/2000 | Vallee |
| 6,410,550 B1 | 6/2002 | Coe |
| 6,890,927 B2 | 5/2005 | Bogle |
| 7,265,119 B2 | 9/2007 | Bogle |
| 7,951,813 B2 | 5/2011 | Abelman |
| 8,158,810 B2 | 4/2012 | Zablocki |
| 8,314,235 B2 | 11/2012 | Dixit |
| 8,558,001 B2 | 10/2013 | Cannizzaro |
| 8,575,353 B2 | 11/2013 | Cannizzaro |
| 8,673,966 B2 | 3/2014 | Graupe |
| 9,000,015 B2 | 4/2015 | Cannizzaro |
| 9,610,299 B2 | 4/2017 | Cannizzaro |
| 9,676,769 B2 * | 6/2017 | Espensen ............... A61P 17/04 |
| 9,987,295 B2 | 6/2018 | Cannizzaro |
| 2004/0138187 A1 | 7/2004 | Reading |
| 2008/0032995 A1 | 2/2008 | Zablocki |
| 2008/0249116 A1 | 10/2008 | Zablocki |
| 2013/0005689 A1 | 1/2013 | Cannizzaro |
| 2017/0266210 A1 | 9/2017 | Cannizzaro |
| 2023/0399307 A1 * | 12/2023 | Blackburn ........... A61K 9/2054 |

FOREIGN PATENT DOCUMENTS

| | | |
|---|---|---|
| CA | 2712750 | 7/2009 |
| CA | 2940269 | 8/2015 |
| WO | 2006058649 A1 | 6/2006 |
| WO | 2007009691 | 1/2007 |
| WO | 2008014497 | 1/2008 |
| WO | 2008124532 | 10/2008 |
| WO | 2009061924 | 5/2009 |
| WO | 2009094028 | 7/2009 |
| WO | 2011014679 | 2/2011 |
| WO | 2013006400 | 1/2013 |

(Continued)

OTHER PUBLICATIONS

Rezvani et al., "Inhibition of Aldehyde Dehydrogenase-2 (ALDH-2) Suppresses Nicotine Self-Administration in Rats," Journal of Drug and Alcohol Research vol. 4 (2015), Article ID 235940, 6 pages; doi:10.4303/jdar/235940.

Diamond et al., "From Ancient Chinese Medicine to a Novel Approach to Treat Cocaine Addiction," CNS & Neurological Disorders—Drug Targets (2015) vol. 14, No. 6.

Volkow et al., "Neurobiologic Advances from the Brain Disease Model of Addiction," N. Engl. J. Med. (2016) 374:363-371.

Yao et al., "Inhibition of aldehyde dehydrogenase-2 suppresses cocaine seeking by generating THP, a cocaine use-dependent inhibitor of dopamine synthesis," Nature Medicine (2010), vol. 16, No. 9.

(Continued)

*Primary Examiner* — John S Kenyon
*Assistant Examiner* — Rehana Ismail
(74) *Attorney, Agent, or Firm* — FisherBroyles, LLP; Adam K. Whiting

(57) ABSTRACT

Disclosed herein are aldehyde dehydrogenase (ALDH-2) inhibitor compounds, such as a compounds of Formula (I) or Formula (II), pharmaceutical compositions comprising these inhibitor compounds, and uses of these compounds and compositions, such as in the methods for safely treating chemical dependency on a substance or condition of addiction, such as alcohol, nicotine, cocaine, opiates, amphetamines, and compulsive eating disorder, and/or anxiety disorder, each individually or concurrent.

10 Claims, No Drawings

(56) References Cited

FOREIGN PATENT DOCUMENTS

| WO | 2013033377 | 3/2013 |
| WO | 2019079209 A1 | 4/2019 |
| WO | 2020076794 A1 | 4/2020 |

OTHER PUBLICATIONS

Darvas et al., "Dopamine dependency for acquisition and performance of Pavlovian conditioned response," Proc. Natl. Acad. Sci. USA (2014), vol. 111 (7): 2764-2769.
Keung et al., (1993) Proc. Natl. Acad. Sci. USA 90, 10008-10012.
Keung et al., (1997) Proc. Natl. Acad. Sci. USA 94, 1675-1679.
Bormann et al.: "Morphine as a conditioned stimulus in a conditioned emotional response paradigm", Psychopharmacology, vol. 112, No. 2-3, Sep. 1993 (Sep. 1, 1993), pp. 277-284.
International Search Report and Written Opinion issued in App. No. PCT/US2023/025166, mailing date Aug. 24, 2023, 11 pages.

\* cited by examiner

ALDH-2 INHIBITOR COMPOUNDS AND METHODS OF USE

CROSS REFERENCE TO RELATED APPLICATIONS

This application claims priority of U.S. Provisional Patent Application No. 63/351,997, filed Jun. 14, 2022, the entirety of which is hereby incorporated by reference herein.

FIELD

The present disclosure relates to novel compounds that selectively inhibit aldehyde dehydrogenase-2 (ALDH-2). The disclosure also relates to pharmaceutical compositions that include the inhibitor compounds and uses of the compounds or compositions in methods for safely treating chemical dependency on a substance or condition of addiction, such as alcohol, nicotine, cocaine, opiates, amphetamines, and compulsive eating disorder, and/or anxiety disorder, each individually or concurrent.

BACKGROUND

Addiction remains a major health problem around the world. The United States Surgeon General has declared substance abuse a national health care crisis that is estimated to have resulted in greater than 3 months reduction in average U.S. life expectancy, 155,000 related deaths per year, 23 million needing treatment, and a $400 billion economic cost annually. See "Facing Addiction in America," Surgeon General's Report, 2016. The Center for Disease Control estimates that illicit drug overdoses killed 64,000 people in the U.S. in 2016, with 14,000 of those deaths resulting from prescription opioid medications.

Inhibition of aldehyde dehydrogenase-2 (ALDH-2) has been shown to reduce pathophysiologic dopamine surge without changing basal dopamine levels in a rat model of cue-induced cocaine relapse-like behavior. See e.g., Yao et al., "Inhibition of aldehyde dehydrogenase-2 suppresses cocaine seeking by generating THP, a cocaine use-dependent inhibitor of dopamine synthesis," *Nature Medicine* (2010), Vol. 16, No. 9; Diamond and Yao, "From Ancient Chinese Medicine to a Novel Approach to Treat Cocaine Addiction," *CNS & Neurological Disorders-Drug Targets* (2015) Vol. 14, No. 6. A recent review concludes that dopamine surge above normal levels is part of the reward circuit common to all drugs of addiction. See e.g., Volkow et al., "Neurobiologic Advances from the Brain Disease Model of Addiction," *N. Engl. J. Med.* (2016) 374:363-371.

A genus of compounds with a structural core related to 2,6-dichloro-N-[4-(2-oxo-1,2-dihydro-pyridin-4-yl)-benzyl]-benzamide, have been shown to inhibit ALDH-2 selectively relative to the monoamine oxidase (MAO) pathway, and exhibit effectiveness in treating rat models of alcohol, nicotine, and cocaine dependency. See e.g., U.S. Pat. Nos. 8,558,001, 8,575,353, 9,000,015, 9,610,299; Int'l Pat. Publ. WO2013/006400; and Rezvani et al., "Inhibition of Aldehyde Dehydrogenase-2 (ALDH-2) Suppresses Nicotine Self-Administration in Rats," (2015) *Journal of Drug and Alcohol Research*, vol. 4: 1-6. The compound 2,6-dichloro-N-[4-(2-oxo-1,2-dihydro-pyridin-4-yl)-benzyl]-benzamide, however, has been found to exhibit high levels of hepatotoxicity in humans. See e.g., O'Malley et al., "Phase 2 Study of ANS-6637, a Specific Inhibitor of ALDH2, in Treatment Seeking Individuals With Alcohol Use Disorder: A Combined Human Laboratory and Outpatient Clinical Trial," (2021) *Neuropsychopharmacology*. Vol. 46: 416-417.

In view of the problematic hepatotoxicity of the ALDH-2 inhibitor, 2,6-dichloro-N-[4-(2-oxo-1,2-dihydro-pyridin-4-yl)-benzyl]-benzamide, there remains a need for ALDH-2 inhibitor compounds with no hepatotoxic liability.

SUMMARY

The present disclosure relates generally to compounds that inhibit ALDH-2, pharmaceutical compositions comprising these compounds, and uses of these compounds for the treatment of addiction and compulsive eating disorder and/or anxiety disorder in mammals. This summary is intended to introduce the subject matter of the present disclosure, but does not cover each and every embodiment, combination, or variation that is contemplated and described within the present disclosure. Further embodiments are contemplated and described by the disclosure of the detailed description, drawings, and claims.

In at least one embodiment, the present disclosure provides a compound of structural Formula

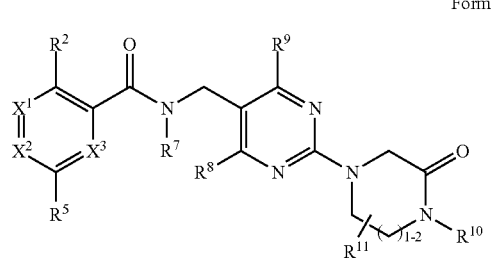

Formula (I)

wherein:
  $X^1$ is N or $CR^3$, $X^2$ is N or $CR^4$, $X^3$ is N or $CR^6$, with the proviso that no more than one of $X^1$, $X^2$, and $X^3$ is N;
  $R^{10}$ is H, optionally substituted $C_{1-6}$ alkyl, —$CH_2OH$, —$CH_2OP(O)(OR^{20})(OR^{21})$;
  $R^{11}$ is H, halogen, optionally substituted $C_{1-6}$ alkyl, or cycloalkyl;
  $R^7$ is H, or optionally substituted $C_{1-6}$ alkyl;
  each of $R^2$, $R^3$, $R^4$, $R^5$, $R^6$, $R^8$, and $R^9$ is independently H, halogen, —$CF_3$, —OH, —$CH_2OH$, —CN, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), —$CH_2OP(O)(OR^{20})(OR^{21})$, —$SO_2NR^{24}R^{25}$; or —$NR^{24}R^{25}$, with the proviso that when $X^1$ is $CR^3$, $X^2$ is $CR^4$, and $X^3$ is $CR^6$, $R^2$ and $R^6$ are not both Cl;
  each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$; and
  each of $R^{24}$ and $R^{25}$ is independently chosen from hydrogen or $C_{1-6}$ alkyl or when combined together with the nitrogen to which they are attached form a heterocycle;

or a pharmaceutically acceptable salt, ester, single stereoisomer, mixture of stereoisomers, or a tautomer thereof.

In at least one embodiment of the compound of structure Formula (I), each of $R^7$, $R^8$, $R^9$, $R^{10}$, and $R^{11}$ are H. In at least one embodiment, each of $R^3$, $R^4$, and $R^5$ are H.

In at least one embodiment of the compound of structure Formula (I), $X^1$ is $CR^3$, $X^2$ is $CR^4$, and $R^3$, $R^4$, and $R^5$ are independently H, Cl, F, $CH_3$, or $CF_3$.

In at least one embodiment of the compound of structure Formula (I), $X^1$ is $CR^3$, $X^2$ is $CR^4$, and $X^3$ is $CR^6$.

In at least one embodiment of the compound of structure Formula (I), $R^2$ is selected from H, Cl, F, or $CH_3$. In at least one embodiment, $R^6$ is selected from H, Cl, F, or $CF_3$.

In at least one embodiment, the present disclosure provides a compound of structural Formula (II):

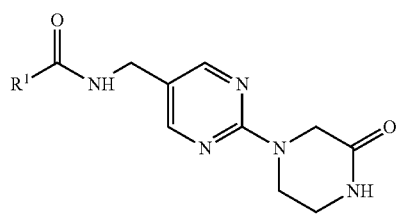

Formula (II)

wherein,
$R^1$ is selected from

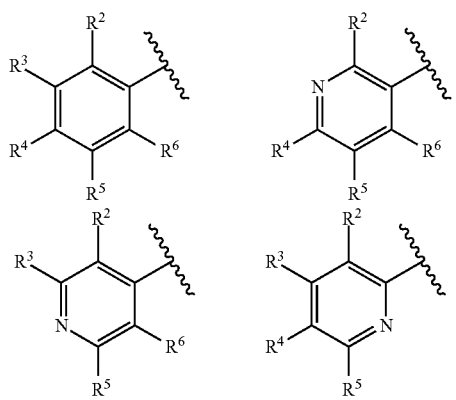

each of $R^2$, and $R^6$, is independently H, Br, Cl, F, $CH_3$, or $CF_3$, with the proviso that $R^2$ and $R^6$ are not both Cl; and each of $R^3$, $R^4$, and $R^5$, is independently H, Br, Cl, F, $CH_3$, $CF_3$, —OH, —$CH_2OH$, —CN, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), —$CH_2OP(O)(OR^{20})$ ($OR^{21}$), —$SO_2NR^{24}R^{25}$; or —$NR^{24}R^{25}$;

or a pharmaceutically acceptable salt, ester, single stereoisomer, mixture of stereoisomers, or a tautomer thereof.

In at least one embodiment of the compound of structural Formula (II), $R^3$, $R^4$, and $R^5$ are independently H, Cl, F, $CH_3$, or $CF_3$. In at least one embodiment, $R^3$, $R^4$, and $R^5$ are H.

In at least one embodiment of the compound of structural Formula (II), $R^2$ is H, Cl, F, or $CH_3$. In at least one embodiment, $R^6$ is H, Cl, F, or $CF_3$.

In at least one embodiment of the compound of structural Formula (II), $R^1$ is selected from:

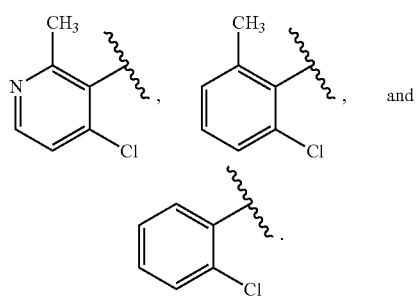

and

In at least one embodiment of the compounds of structural Formula (I) or structural Formula (II) of the present disclosure, the compound is selected from compounds (1a), (1b), and (1c), the structures of which are depicted below in Table 1, including pharmaceutically acceptable salts, esters, single stereoisomers, mixtures of stereoisomers, or tautomers thereof.

TABLE 1

Exemplary ALDH-2 Inhibitor Compounds

| | |
|---|---|
| ![1a structure] | (1a) |
| ![1b structure] | (1b) |
| ![1c structure] | (1c) |

In at least one embodiment, the present disclosure provides a pharmaceutical composition comprising a therapeutically effective amount of the compound of structural Formula (I) or Formula (II), or a pharmaceutically acceptable salt, ester, single stereoisomer, mixture of stereoisomers, or a tautomer thereof, and a pharmaceutically acceptable carrier.

In at least one embodiment, the present disclosure provides a method of treating chemical dependency on a substance or condition of addiction or abuse comprising administering a compound of structural Formula (I) or Formula (II) (e.g., a compound of Table 1), or a pharmaceutically acceptable salt, ester, single stereoisomer, mixture of stereoisomers, or a tautomer thereof, or administering a pharmaceutical composition comprising a therapeutically effective amount of the compound of structural Formula (I) or Formula (II), or a pharmaceutically acceptable salt, ester, single stereoisomer, mixture of stereoisomers, or a tautomer thereof. In at least one embodiment, substance or condition of addiction or abuse is selected from the group consisting of alcohol, nicotine, cocaine, opiates, amphetamines, compulsive eating disorder, and anxiety disorder, each individual or concurrent.

In at least one embodiment, the present disclosure provides a method of treating compulsive eating comprising administering to a human patient a compound of structural Formula (I) or Formula (II), or a pharmaceutically acceptable salt, ester, single stereoisomer, mixture of stereoisomers, or a tautomer thereof, or administering a pharmaceutical composition comprising a therapeutically effective amount of the compound of structural Formula (I) or Formula (II), or a pharmaceutically acceptable salt, ester, single stereoisomer, mixture of stereoisomers, or a tautomer thereof.

In at least one embodiment, the present disclosure provides a method of treating a compulsive eating disorder comprising administering to a human patient a compound of structural Formula (I) or Formula (II), or a pharmaceutically acceptable salt, ester, single stereoisomer, mixture of stereoisomers, or a tautomer thereof, or administering a pharmaceutical composition comprising a therapeutically effective amount of the compound of structural Formula (I) or Formula (II), or a pharmaceutically acceptable salt, ester, single stereoisomer, mixture of stereoisomers, or a tautomer thereof.

In at least one embodiment, the present disclosure provides a method of treating anxiety disorder comprising administering to a human patient a compound of structural Formula (I) or Formula (II), or a pharmaceutically acceptable salt, ester, single stereoisomer, mixture of stereoisomers, or a tautomer thereof, or administering a pharmaceutical composition comprising a therapeutically effective amount of the compound of structural Formula (I) or Formula (II), or a pharmaceutically acceptable salt, ester, single stereoisomer, mixture of stereoisomers, or a tautomer thereof.

In at least one embodiment, the present disclosure provides an ALDH-2 inhibitor comprising a compound of structural Formula (I) or Formula (II), or a pharmaceutically acceptable salt, ester, single stereoisomer, mixture of stereoisomers, or a tautomer thereof, for use in therapy, for use as a medicament, for use in treating chemical dependency on a substance, for use in treating a condition of addiction or abuse, for use in treating a compulsive eating disorder, or for use in treating an anxiety disorder.

In at least one embodiment, the present disclosure provides an ALDH-2 inhibitor comprising a compound of structural Formula (I) or Formula (II), or a pharmaceutically acceptable salt, ester, single stereoisomer, mixture of stereoisomers, or a tautomer thereof, for use in the manufacture of a pharmaceutical composition or a medicament for the treatment of chemical dependency on a substance, for use in treating a condition of addiction or abuse, for use in treating a compulsive eating disorder, or for use in treating an anxiety disorder.

DETAILED DESCRIPTION

It is to be understood that the detailed descriptions provided herein, including the drawings, are exemplary and explanatory only and are not restrictive of this disclosure. The description is not limited to the specific compounds, compositions, methods, techniques, protocols, cell lines, assays, and reagents disclosed herein, as these may vary, but is also intended to encompass known variants of these specific embodiments.

It is also to be understood that the terminology used herein is intended to describe particular embodiments and is in not intended to limit the scope as set forth in the appended claims. For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Further, it is understood that where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50" includes "2 to 25", "5 to 20", "25 to 50", "1 to 10", etc.

Abbreviations, Definitions and General Parameters

As used in the present specification, the following words and phrases are generally intended to have the meanings as set forth below, except to the extent that the context in which they are used indicates otherwise.

The term "ALDH-2 inhibitor" as used herein includes any compound that selectively inhibits the enzyme aldehyde dehydrogenase 2. Besides the compounds of structural Formulas (I) and (I) of the present disclosure, exemplary ALDH-2 inhibitor compounds include the isoflavone compound, daidzein (see e.g., U.S. Pat. Nos. 5,624,910, and 6,121,010), its structurally related isoflavone derivative compounds (see e.g., U.S. Pat. Nos. 7,951,813, 8,158,810, and 8,673,966; Int'l Pat. Publ. Nos. WO2008/014497, WO2008/124532, WO2009/061924, WO2009/094028, and WO2013/033377), and the compounds, which are structurally unrelated to the isoflavones, such as 2,6-dichloro-N-[4-(2-oxo-1,2-dihydro-pyridin-4-yl)-benzyl]-benzamide (see e.g., U.S. Pat. Nos. 8,558,001, 8,575,353, 9,000,015, 9,610, 299; Int'l Pat. Publ. WO2013/006400).

The term "addiction" as used herein includes any substance use disorder including, but not limited to, substance misuse, substance dependence, substance addiction, and/or condition of addiction, such as a compulsive or binge eating disorder, and/or an anxiety disorder, each individually or concurrent. Exemplary substances of misuse, dependence, and/or addiction, include but are not limited to, alcohol, nicotine, cocaine, opiates, and amphetamines.

The term "alcohol" as used herein in the context of addictive substances that may be consumed by humans refers to ethanol ("EtOH").

The term "anxiety disorder" as used herein refers to anxiety that does not go away, gets worse over time, and which results in symptoms that can interfere with daily activities such as job performance, schoolwork, and relationships. Exemplary anxiety disorders include but are not limited to generalized anxiety disorder, panic disorder, social anxiety disorder, and various phobia-related disorders.

The term "compulsive eating disorder" or "binge eating disorder" as used herein refers to a disorder characterized by recurrent binge eating episodes during which a person feels a loss of control and marked distress over his or her eating, and results in the person becoming overweight or obese.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "unit dosage form" refers to physically discrete units suitable as unitary dosages for human subjects and other mammals, each unit containing a predetermined quantity of active ingredient that produces the desired therapeutic effect, in association with a suitable pharmaceutical excipient (e.g., a tablet, capsule, or ampoule).

The term "active ingredient" refers to a compound in a pharmaceutical composition that has a pharmacological effect when administered to an organism (e.g., a mammal) and is intended to encompass not only the compound but also the pharmaceutically acceptable salts, pharmaceutically acceptable esters, hydrates, polymorphs, and prodrugs of such compound.

The term "prodrug" refers to a compound that includes a chemical group which, in vivo, can be converted and/or split off from the remainder of the molecule to provide for the active drug, a pharmaceutically acceptable salt thereof, or a biologically active metabolite thereof.

The term "treatment" or "treating" means any administration of a compound of the disclosure to a mammal having a disease or disorder, or a mammal susceptible to a disease or disorder, for purposes including:
  (i) preventing the disease, that is, causing the clinical symptoms of the disease not to develop;
  (ii) inhibiting the disease, that is, arresting the development of clinical symptoms; and/or
  (iii) relieving the disease, i.e., causing the regression of clinical symptoms.

The term "during treatment" as used herein refers to the time period after administration of a therapeutically effective amount of a compound to a subject for treatment of a disease or disorder until the time at which the amount of the compound in the subject has decreased to a level below what is therapeutically effective.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
  (i) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
  (ii) an alkyl group as defined above that is interrupted by 1-10 atoms (e.g. 1, 2, 3, 4, or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
  (iii) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:
  (i) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or (ii) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —$NR^a$, where $R^a$ is chosen from hydrogen, optionally substituted alkyl, cycloalkyl, cycloalkenyl, aryl, heteroaryl and heterocyclyl; or (iii) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—$CH(NH_2)CH_2$—), methylaminoethylene (—$CH(NHMe)CH_2$—), 2-carboxypropylene isomers (—$CH_2CH(CO_2H)CH_2$—), ethoxyethyl (—$CH_2CH_2O$—$CH_2CH_2$—), ethylmethylaminoethyl (—$CH_2CH_2$—$N(CH_3)$—$CH_2CH_2$—), 1-ethoxy-2-(2-ethoxy-ethoxy)ethane (—$CH_2CH_2O$—$CH_2CH_2$—$OCH_2CH_2$—$OCH_2CH_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH=$CH_2$), 1-propylene (or allyl, —$CH_2CH$=$CH_2$), isopropylene (—$C(CH_3)$=$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 10 carbon atoms, e.g. 2 to 6 carbon atoms) and having from 1 to 6 carbon-carbon triple bonds e.g. 1, 2, or 3 carbon-carbon triple bonds. Typical alkynyl groups include ethynyl (—C≡CH), propargyl (or propynyl, —C≡$CCH_3$), and the like. In the event alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, $CF_3$, amino, substituted amino, cyano, or —$S(O)_nR^a$, in which $R^a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo [2.2.1]heptane, or cyclic alkyl groups to which is fused an aryl group, for example indan, and the like.

The term "cycloalkenyl" refers to cyclic alkyl groups of from 3 to 20 carbon atoms having a single cyclic ring or multiple condensed rings and having at least one double bond and preferably from 1 to 2 double bonds.

The terms "substituted cycloalkyl" and "substituted cycloalkenyl" refer to cycloalkyl or cycloalkenyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "alkoxycarbonylamino" refers to a group —NHC(O)OR in which R is optionally substituted alkyl.

The term "alkyl amine" refers to R—$NH_2$ in which R is optionally substituted alkyl.

The term "dialkyl amine" refers to R—NHR in which each R is independently an optionally substituted alkyl.

The term "trialkyl amine" refers to $NR_3$ in which R each R is independently an optionally substituted alkyl.

The term "azido" refers to a group

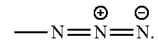

The term "hydroxyl" or "hydroxyl" refers to a group —OH.

The term "arylthio" refers to the group —S-aryl.

The term "heterocyclylthio" refers to the group —S-heterocyclyl.

The term "alkylthio" refers to the group —S-alkyl.

The term "aminosulfonyl" refers to the group —$SO_2$NRR, wherein each R is independently selected from the group consisting of hydrogen, alkyl, cycloalkyl, aryl, heteroaryl and heterocyclyl.

Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclyloxy, hydroxyamino, alkoxyamino, nitro, —SO-alkyl, —SO-aryl, —SO-heteroaryl, —SO$_2$-alkyl, SO$_2$-aryl and —SO$_2$-heteroaryl.

The term "aminocarbonylamino" refers to the group —NR$^c$C(O)NRR, wherein R$^c$ is hydrogen or alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl.

The term "heterocyclooxy" refers to the group —O-heterocyclyl.

The term "alkoxyamino" refers to the group —NHOR in which R is optionally substituted alkyl.

The term "hydroxyamino" refers to the group —NHOH.

The term "heteroaryl" refers to a group comprising single or multiple rings comprising 1 to 15 carbon atoms and 1 to 4 heteroatoms selected from oxygen, nitrogen, and sulfur within at least one ring. The term "heteroaryl" is generic to the terms "aromatic heteroaryl" and "partially saturated heteroaryl." The term "aromatic heteroaryl" refers to a heteroaryl in which at least one ring is aromatic. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, and the like.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl," "heterocycle," or "heterocyclic" refers to a monoradical saturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$— heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" or "oxo" refers to a group —C(O)—.

The term "thiocarbonyl" refers to a group —C(S)—.

The term "carboxy" refers to a group —C(O)—OH.

The term "optional" or "optionally" mean that the subsequently described event or circumstance may or may not occur, and that the description includes instances where said event or circumstance occurs and instances in which it does not.

The term "substituted" includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to substituted aryl-(substituted aryl)-substituted aryl.

A compound of a given formula (e.g. the "compound of Formula (I)") is intended to encompass the compounds of the disclosure, and the pharmaceutically acceptable salts, pharmaceutically acceptable esters, hydrates, polymorphs, and prodrugs of such compounds.

Additionally, the compounds of the disclosure may possess one or more asymmetric centers and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

The term "isomers" means different compounds that have the same molecular formula. Isomers include stereoisomers, enantiomers, and diastereomers.

The term "stereoisomers" means isomers that differ only in the way the atoms are arranged in space.

The term "enantiomers" means a pair of stereoisomers that are non-superimposable mirror images of each other. A 1:1 mixture of a pair of enantiomers is a "racemic" mixture. The term "(±)" is used to designate a racemic mixture where appropriate.

The term "diastereoisomers" means stereoisomers that have at least two asymmetric atoms, but which are not mirror-images of each other.

Absolute stereochemistry is specified herein according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or levorotary) that they rotate the plane of polarized light at the wavelength of the sodium D line.

Some of the compounds of the present disclosure exist as "tautomeric isomers" or "tautomers." "Tautomeric isomers" or "tautomers" are isomers that are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

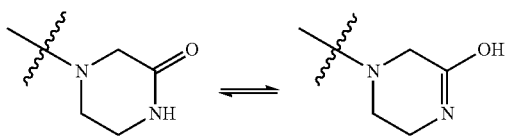

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by combining a compound and a solvent.

The term "hydrate" refers to the complex formed by combining a compound and water.

The term "pharmaceutically acceptable salt" of a given compound refers to salts that retain the biological effectiveness and properties of the given compound, and which are not biologically or otherwise undesirable. In many cases, the compounds of this disclosure are capable of forming pharmaceutically acceptable acid and/or base salts by virtue of the presence of amino and/or carboxyl groups or groups similar thereto.

Pharmaceutically acceptable base addition salts can be prepared from inorganic and organic bases. Salts derived from inorganic bases include, by way of example only, sodium, potassium, lithium, ammonium, calcium, and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts also may be prepared from inorganic and organic acids. Salts derived from inorganic acids include the salts of hydrochloric acid, hydrobromic acid, sulfuric acid, nitric acid, phosphoric acid, and the like, and include, but are not limited to, chloride, chlorate, bromide, bromate, nitrite, nitrate, phosphite, phosphate, sulfate, and hemisulfate salts. Salts derived from organic acids include the salts of acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The terms "pharmaceutically acceptable carrier" or "pharmaceutically acceptable excipient" as used herein includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Any formula or structure given herein, including Formula (I) and Formula (II), is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as $^3H$, $^{13}C$, and $^{14}C$ are incorporated. Such isotopically labelled compounds may be useful in metabolic studies, reaction kinetic studies, detection, or imaging techniques, such as positron emission tomography (PET) or single-photon emission computed tomography (SPECT) including drug or substrate tissue distribution assays, or in radioactive treatment of patients.

Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}F$ labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula (I) or Formula (II).

The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen," the position is understood to have hydrogen at its natural abundance isotopic composition. Accordingly, in the compounds of this invention any atom specifically designated as a deuterium (D) is meant to represent deuterium.

In the description, including the Examples, all temperatures are in degrees Celsius (° C.), unless otherwise stated, and abbreviations and acronyms have the following meanings listed in Table 2 (below).

TABLE 2

| Abbreviation | Meaning |
|---|---|
| AcOH | Acetic acid |
| ALDH-2 | Human mitochondrial aldehyde dehydrogenase |
| BHA | Butylated hydroxy anisole |
| Boc | tert-Butoxycarbonyl |
| (Boc)$_2$O | Di(tert-butyl) carbonate |
| ° C. | Degree Celsius |
| Cbz | Benzyl carbamate |
| cm | centimeter |
| Cs$_2$CO$_3$ | Cesium carbonate |
| DA | Dopamine |
| DBU | 1,8-Diazabicyclo[5.4.0]undec-7-ene |
| DCC | Dicyclohexyl carbodiimide |
| DCM | Dichloromethane |
| DIC | Diisopropyl carbodiimide |
| DIEA | N,N-Diisopropylethylamine |
| DIPEA | Diisopropylethylamine |
| DMAP | 4-Dimethylaminopyridine |
| DMF | Dimethylformamide |
| DMF | Dimehtylformamide |
| DMSO | Dimethylsulfoxide |
| EDTA | Ethylenediaminetetraacetic acid |
| equiv/eq | Equivalents |
| EtOAc | Ethyl acetate |
| EtOH | Ethanol |
| g | Grams |
| HATU | (1-[Bis(dimethylamino)methylene]-1H-1,2,3-triazolo[4,5-b]pyridinium 3-oxide hexafluorophosphate |
| HPLC | High-performance liquid chromatography |
| hrs/h | Hours |
| Hz | Hertz |
| IC$_{50}$ | The half maximal inhibitory concentration |
| IIDQ | 1-Isobutoxycarbonyl-2-isobutoxy-1,2-dihydro quinone |
| ip | Intraperitoneal |
| iv | Intravenous |
| J | Coupling constant |
| K$_2$CO$_3$ | Potassium carbonate |
| Kg | Kilogram |
| KOAc | Potassium acetate |
| KOtBu | Potassium tert-Butoxide |
| L | Liter |
| LC-MS | Liquid chromatography-mass spectrometry |
| LG | Leaving group |
| M | Molar |
| m/z | mass-to-charge ratio |
| M+ | Mass peak |
| M + H | Mass peak plus hydrogen |
| M + Na | Mass peak plus sodium |
| MAO | Monoamine oxidase |
| Me | Methyl |
| MeOH | Methanol |
| mg | Milligram |
| MHz | Megahertz |

TABLE 2-continued

| Abbreviation | Meaning |
| --- | --- |
| min | Minute |
| mL (or ml) | Milliliter |
| mM | Millimolar |
| mmol | Millimole |
| MS | Mass spectroscopy |
| MTBE | Methyl tert-butyl ether |
| MW | Microwave |
| $Na_2CO_3$ | Sodium carbonate |
| $NaBH_4$ | Sodium borohydride |
| NAD | Nicotinamide Adenine Dinucleotide |
| NaOH | Sodium hydroxide |
| NMM | N-Methylmorpholine |
| NMP | N-Methyl-2-pyrrolidone |
| NMR | Nuclear magnetic resonance |
| PG | Protecting group |
| Ph | Phenyl |
| q.s. | Quantity sufficient to achieve a stated function |
| rt | Room temperature |
| S | Second |
| SC | Subcutaneous |
| SEM | Standard error of means |
| TEA | Triethylamine |
| THF | Tetrahydrofuran |
| TLC | Thin layer chromatography |
| TMS | Trimethylsily1 |
| TMSCl | Trimethysilyl chloride |
| Tris | tris(hydroxymethyl)aminomethane |
| δ | Chemical shift |
| μg | Microgram |
| μL (or μl) | Microliter |
| μM | Micromolar |
| μmol | Micromole |

ALDH-2 Inhibitor Compounds

Compounds that act as selective inhibitors of ALDH-2 have been shown to reduce pathophysiologic dopamine surge. See e.g., Yao et al., "Inhibition of aldehyde dehydrogenase-2 suppresses cocaine seeking by generating THP, a cocaine use-dependent inhibitor of dopamine synthesis," *Nature Medicine* (2010), Vol. 16, No. 9; Diamond and Yao, "From Ancient Chinese Medicine to a Novel Approach to Treat Cocaine Addiction," *CNS & Neurological Disorders—Drug Targets* (2015) Vol. 14, No. 6. Selective inhibitors of ALDH-2 have also demonstrated the ability to suppress self-administration of nicotine in rats. See e.g., Rezvani et al., "Inhibition of Aldehyde Dehydrogenase-2 (ALDH-2) Suppresses Nicotine Self-Administration in Rats," (2015) *Journal of Drug and Alcohol Research*, vol. 4: 1-6; Kim et al. "Brain Microdialysis Coupled to LC-MS/MS Revealed That CVT-10216, a Selective Inhibitor of Aldehyde Dehydrogenase 2, Alters the Neurochemical and Behavioral Effects of Methamphetamine," (2021) *ACS Chem Neurosci*, Vol. 12: 1552-1562; and U.S. Pat. Nos. 8,558,001, 8,575,353, 9,000,015, 9,610,299; Int'l Pat. Publ. WO2013/006400. The novel ALDH-2 inhibitor compounds provided in the present disclosure have been shown to selectively inhibit ALDH-2 in preclinical assays and to exhibit characteristics of lowered hepatoxic liability. Accordingly, the compounds of the present disclosure can be useful for the treatment of conditions responsive to the selective inhibition of ALDH-2 and the reduction of pathophysiologic dopamine surge. Such uses can include the reduction and/or prevention of addiction in mammals to substances or conditions of abuse or addiction including alcohol, nicotine, cocaine, methamphetamine, opioids, compulsive eating disorder, and/or anxiety disorder, each individually or concurrently.

In at least one embodiment, the present disclosure provides an ALDH-2 inhibitor compound of structural Formula (I):

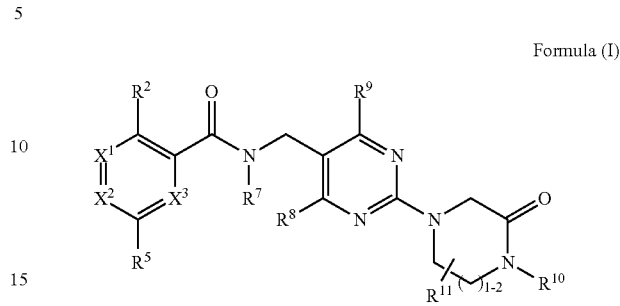

Formula (I)

wherein:

$X^1$ is N or $CR^3$, $X^2$ is N or $CR^4$, $X^3$ is N or $CR^6$, with the proviso that no more than one of $X^1$, $X^2$, and $X^3$ is N;

$R^{10}$ is H, optionally substituted $C_{1-6}$ alkyl, —$CH_2OH$, —$CH_2OP(O)(OR^{20})(OR^{21})$;

$R^{11}$ is H, halogen, optionally substituted $C_{1-6}$ alkyl, or cycloalkyl;

$R^7$ is H, or optionally substituted $C_{1-6}$ alkyl;

each of $R^2$, $R^3$, $R^4$, $R^5$, $R^6$, $R^8$, $R^9$ is independently H, halogen, —$CF_3$, —OH, —$CH_2OH$, —CN, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), —$CH_2OP(O)(OR^{20})(OR^{21})$, —$SO_2NR^{24}R^{25}$; or —$NR^{24}R^{25}$, with the proviso that when $X^1$ is $CR^3$, $X^2$ is $CR^4$, and $X^3$ is $CR^6$, $R^2$ and $R^6$ are not both Cl;

each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$; and each of $R^{24}$ and $R^{25}$ is independently chosen from hydrogen or $C_{1-6}$ alkyl or when combined together with the nitrogen to which they are attached form a heterocycle;

or a pharmaceutically acceptable salt, ester, single stereoisomer, mixture of stereoisomers, or a tautomer thereof.

As illustrated by the exemplary compounds (1a), (1b), and (1c), a wide range of specific ALDH-2 inhibitor compound structures within structural Formula (I) are contemplated, including pharmaceutically acceptable salts, esters, single stereoisomers, mixtures of stereoisomers, or tautomers of the compounds, and compounds having one or more of the following structural features: (i) each of $R^7$, $R^8$, $R^9$, $R^{10}$, $R^{11}$, and $R^{12}$ are H; (ii) each of $R^3$, $R^4$, and $R^5$ are H; (iii) $X^1$ is $CR^3$, $X^2$ is $CR^4$, and $R^3$, $R^4$, and $R^5$ are independently selected from H, Cl, F, $CH_3$, and $CF_3$; (iv) $X^1$ is $CR^3$, $X^2$ is $CR^4$, and $X^3$ is $CR^6$; (v) $R^2$ is selected from H, Cl, F, or $CH_3$; and/or (vi) at least one embodiment, $R^6$ is selected from H, Cl, F, or $CF_3$.

In at least one embodiment, the present disclosure provides an ALDH-2 inhibitor compound of structural Formula (II):

Formula (II)

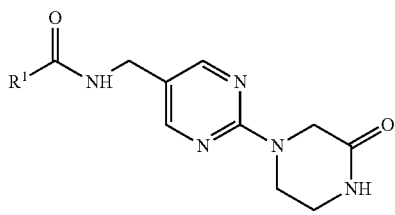

wherein,

R¹ is selected from

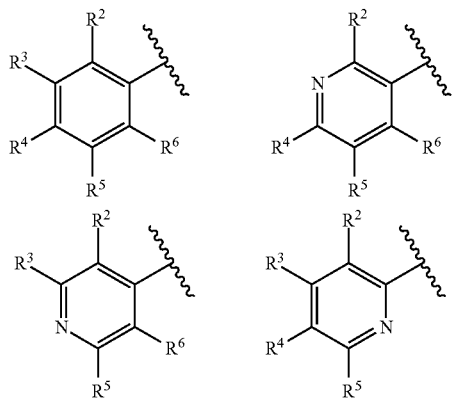

each of R², and R⁶, is independently H, Br, Cl, F, CH₃, or CF₃, with the proviso that R² and R⁶ are not both Cl; and each of R³, R⁴, and R⁵, is independently H, Br, Cl, F, CH₃, CF₃, —OH, —CH₂OH, —CN, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—(C₁ to C₆-alkyl)-O—(C₁ to C₆-alkyl), —CH₂OP(O)(OR²⁰)(OR²¹), —SO₂NR²⁴R²⁵; or —NR²⁴R²⁵;

or a pharmaceutically acceptable salt, ester, single stereoisomer, mixture of stereoisomers, or a tautomer thereof.

As illustrated by the exemplary compounds (1a), (1b), and (1c) (structures depicted in Table 1) a wide range of specific ALDH-2 inhibitor compound structures within structural formula (II) are contemplated, including pharmaceutically acceptable salts, esters, single stereoisomers, mixtures of stereoisomers, or tautomers of the compounds, and compounds having one or more of the following structural features: (i) R³, R⁴, and R⁵ are independently H, Cl, F, CH₃, or CF₃; (ii) R³, R⁴, and R⁵ are H; (iii) R² is H, Cl, F, or Cl₃; (vi) R⁶ is H, Cl, F, or CF₃; and/or (iv) R¹ is selected from:

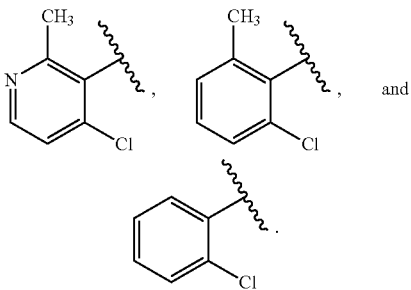

The ALDH-2 inhibitor compounds of structural Formulas (I) and (II) can be prepared from readily available starting materials using methods and procedures known in the art. In particular, the present disclosure provides general synthetic strategies for preparing compounds of structural Formula (I) and structural Formula (II), and also exemplifies specific synthesis protocols that can be used to prepare the exemplary compounds (1a), (1b), and (1c) described herein and listed in Table 1.

Briefly, the compounds of Formula (I) or (II) may be prepared according to the synthetic sequence shown in Scheme A Scheme A

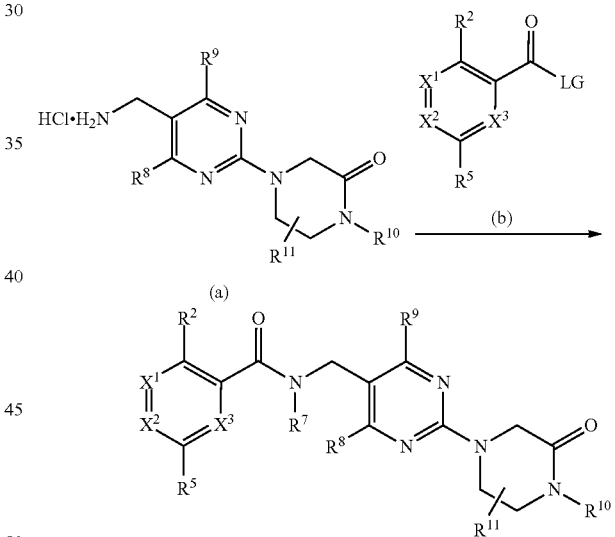

wherein, substituents R¹ through R¹², X¹ through X³ are as defined herein, and LG is a leaving group (e.g., halo, hydroxyl, alkoxy, OSO₂ CF₃, N₂⁺, etc.). The Scheme A reactants (a) and (b) are commercially available or can be prepared as described in the Examples below, or by means well known in the art. In general, the reactants (a) and at least one molar equivalent, and preferably a slight excess (e.g., 1.2 to 1.5 molar equivalents) of (b), as shown in Scheme A, are combined under standard reaction conditions in an inert solvent, such as dichloromethane (DCM) or dimethylformamide (DMF), at a temperature of about 0° C. to about 25° C. until the reaction is complete, generally about 30 minutes to about 2 hours. Standard reaction conditions further comprise the use of a molar excess of suitable base, such as triethylamine (TEA), diisopropylethylamine (DIPEA), N-methylmorpholine (NMM), sodium or potassium hydroxide, or pyridine, or in some cases where LG is hydroxyl, a peptide coupling reagent, such as O-(7-azabenzotriazol-1-yl)-N,N,N',N'-tetra methyluronium hexafluorophosphate (HATU), may be used. When the reaction is substantially complete, the product is subjected, if necessary, to a deprotection sequence under standard reaction conditions (e.g., THF, CH$_2$Cl$_2$, or the like, a molar excess of acid such as acetic acid, formic acid, trifluoroacetic acid, or the like as described herein) to yield isolated by conventional means.

Phosphate ester derivatives of compounds of Formula (I) or Formula (II) at the R$^{11}$ substituent may be prepared as shown below in the synthetic sequence of Scheme B.

herein) yields phosphate ester (h). Phosphate esters of ALDH-2 inhibitor compounds have been shown to be useful as prodrugs via in vivo hydrolysis of the phosphate ester. See e.g., U.S. Pat. No. 8,558,001, which is hereby incorporated by reference herein.

It will be appreciated that where typical or preferred process conditions (i.e., reaction temperatures, times, mole ratios of reactants, solvents, pressures, etc.) in the Examples herein, other process conditions can also be used unless otherwise stated. Optimum reaction conditions may vary with the particular reactants or solvent used, but such conditions can be determined by one skilled in the art by routine optimization procedures. Additionally, as will be

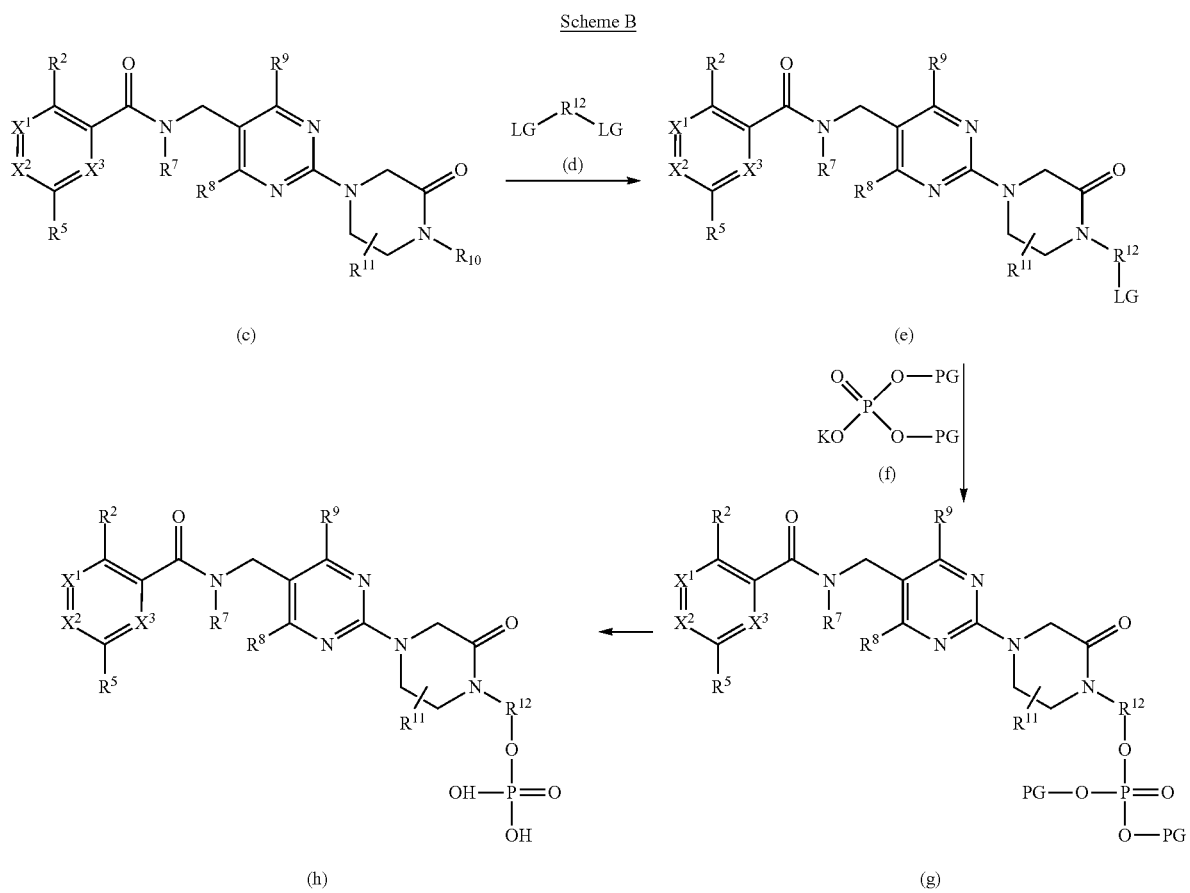

Scheme B

For example, phosphate ester derivatives (h) can be prepared according to the synthetic sequence of Scheme B by the alkylation of a pyridin-2(1H)-one (c) with at least one equivalent, and preferably a slight excess (e.g., 1.2 to 1.5 molar equivalents) of linker (d), wherein R$^{12}$ is an optionally substituted alkylene moiety of 1-6 carbon atoms, and at least one equivalent, and preferably a slight excess (e.g., 1.2 to 2 molar equivalents) of a suitable base such as triethylamine (TEA), diisopropylethylamine (DIPEA), N-methylmorpholine (NMM), or pyridine under standard reaction conditions to yield the alkylated pyridin-2(1H)-one derivative (e). This derivative (e) can subsequently be used to O-alkylate a molar excess (e.g., 1.2 to 5 molar equivalents) of phosphate diester (f) to yield the corresponding phosphate triester (g). Deprotection of phosphate triester (g) under standard conditions (e.g., CH$_3$CN/H$_2$O or the like, a molar excess of acid such as acetic acid or the like with heating, as described apparent to those skilled in the art, conventional protecting groups may be necessary to prevent certain functional groups from undergoing undesired reactions. For example, a protecting group may be used to allow a functional group (such as O, S, or N) to be temporarily blocked so that a reaction can be carried out selectively at another reactive site in a multifunctional compound. Protecting groups useful in syntheses of the present disclosure are well known in the art and include those described in detail in *Protective Groups in Organic Synthesis*, Fourth Ed., Greene, T. W. and Wuts, P. G., Eds., John Wiley & Sons, New York: 2007, the entire contents of which are hereby incorporated by reference, and references cited therein.

As noted above, starting materials for the synthetic reaction Scheme A are as disclosed in the Examples herein, are commercially available, or are generally known compounds that can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemie or Sigma (St. Louis, Missouri, USA). Others may be prepared by procedures, or obvious modifications thereof, described in standard reference texts such as *Fieser and Fieser's Reagents for Organic Synthesis*, Volumes 1-15 (John Wiley, and Sons, 1991), *Rodd's Chemistry of Carbon Compounds*, Volumes 1-5, and Supplementals (Elsevier Science Publishers, 1989), *Organic Reactions*, Volumes 1-40 (John Wiley, and Sons, 1991), *March's Advanced Organic Chemistry*, (John Wiley, and Sons, 5th Edition, 2001), and *Larock's Comprehensive Organic Transformations* (VCH Publishers Inc., 1989).

Uses and Methods of Treatment

The present disclosure also provides uses of the ALDH-2 inhibitor compounds of structural Formulas (I) or (II) of the present disclosure, including uses in pharmaceutical compositions, which compositions can be used in methods for treatment and/or prevention of addiction or conditions of substance abuse in mammals, including addiction to or conditions of abuse of alcohol, nicotine, cocaine, methamphetamine, and/or opioids, and/or a compulsive eating disorder, and/or an anxiety disorder, each individually or concurrently. The primary factor in the development of conditions of abuse or addiction is neurophysiologic reinforcement (reward). Animal studies suggest the existence of at least one central reward-reinforcement pathway for drug self-administration in the human brain (Volkow 2016). This pathway involves dopaminergic neurons that originate in the ventral tegmental area (VTA) and project into the nucleus accumbens (NAc) and forebrain. Release of dopamine from these neurons onto the dopamine receptors in the NAc produces positive reinforcement.

All known addictive drugs activate reward regions in the brain by causing sharp increases in the release of dopamine (DA) to elicit a reward signal that triggers associative learning or conditioning. In this type of Pavlovian learning, repeated experiences of reward become associated with the environmental stimuli that precede them. With repeated exposure to the same reward, dopamine cells stop firing in response to the reward itself and instead fire in an anticipatory response to the conditioned stimuli (referred to as "cues") that in a sense predict the delivery of the reward. Addictive drugs circumvent natural satiation of a 'natural reward' such as food or sex by directly increasing dopamine—a factor that may explain why compulsive behaviors are more likely to emerge when people use drugs than when they pursue a natural reward.

It is well-established that cocaine and other addictive substances or conditions stimulate an increase in DA levels in the NAc, which appears to mediate reward or reinforcement processes in brain (DiChiara 1988) (Boileau 2003) (Tizabi 2002). Volkow and Koob (Volkow 2016) provide evidence that a surge of dopamine (DA) drives craving and addictive behavior through reward circuits (Feltenstein and See 2008). Conditioned responses that trigger craving for addictive substances motivate behaviors that often lead to heavy substance use, and these strong cravings can persist long after use has stopped (Volkow 2016).

While not wishing to be bound by theory, ALDH-2 inhibitors, such as the compounds of structural Formulas (I) and (II) of the present disclosure, are effective in reducing or preventing surges in dopamine levels caused by administration of a substance or conditions of abuse including alcohol, nicotine, cocaine, methamphetamine, opioids, compulsive eating disorder, and/or anxiety disorder. Therefore, ALDH-2 inhibitors of the present disclosure can be administered to a mammal as a method to treat, reduce, and/or prevent addiction in a mammal receiving the treatment.

Accordingly, it is contemplated that the ALDH-2 inhibitors comprising a compound of structural Formula (I) or Formula (II), or a pharmaceutically acceptable salt, ester, single stereoisomer, mixture of stereoisomers, or a tautomer of such a compound, can be used in therapy. For example, the inhibitor compounds of the present disclosure can be used as a pharmaceutical composition or medicament, and that these compositions can be used in treating conditions affected by inhibition of ALDH-2. For example, the use in the treatment of chemical dependency on a substance, use in treatment of a condition of addiction or abuse, use in treatment of a compulsive eating disorder, or use in treatment of an anxiety disorder.

Further, the present disclosure also contemplates the use of the ALDH-2 inhibitors comprising a compound of structural Formula (I) or Formula (II), or a pharmaceutically acceptable salt, ester, single stereoisomer, mixture of stereoisomers, or a tautomer of such a compound, in the manufacture of pharmaceutical compositions or medicaments. For example, pharmaceutical compositions or medicaments for the treatment of chemical dependency on a substance, for use in treating a condition of addiction or abuse, for use in treating a compulsive eating disorder, or for use in treating an anxiety disorder.

In at least one embodiment, it is contemplated that the methods can be used to treat any mammal that needs therapy for a condition such as addiction. In particular it is contemplated that the method can be used wherein the mammal is a human. Accordingly, in at least one embodiment, the present disclosure provides a method for treatment, or prevention of the acquisition of, addiction to substances or conditions of abuse in a mammal wherein the method comprises administering to the mammal a therapeutically effective amount of an ALDH-2 inhibitor, wherein the ALDH-2 inhibitor is a compound of structural Formula (I) or Formula (II), or a pharmaceutically acceptable salt, ester, single stereoisomer, mixture of stereoisomers, or a tautomer of such a compound. In at least one embodiment, the compound administered can be a compound selected from compounds (1a), (1b), and (1c), or a pharmaceutically acceptable salt, ester, single stereoisomer, mixture of stereoisomers, or a tautomer thereof.

In the at least one embodiment of the method, the step of administering the ALDH-2 inhibitor can comprise administering a pharmaceutical composition, wherein the pharmaceutical composition comprises the medication, the ALDH-2 inhibitor, and a pharmaceutically acceptable carrier.

In some embodiments of such methods of treatment, the method comprises self-administering a therapeutically effective dose of an ALDH-2 inhibitor to reduce the urge to use a substance of abuse such as alcohol, nicotine, cocaine, methamphetamine, opioids, and food. In some embodiments, it is contemplated that the ALDH-2 inhibitor compound in the form of a pharmaceutical composition is administered (including self-administered) as a once- or a twice-a-day dose. In some embodiments, the once-a-day dose is in a formulation (e.g., a tablet), that is self-administered by the subject or patient.

In some embodiments for treatment of addiction, it is contemplated that administration of the ALDH-2 inhibitor compound to the subject can continue for at least 1 month, at least 3 months, at least 6 months, at least 1 year, or forever.

In various embodiments of the methods disclosed herein for the safe treatment, or prevention of the acquisition, of addiction to substances or conditions of abuse in a mammal, the ALDH-2 inhibitor has low hepatotoxic liability and/or is not hepatotoxic. It has been reported that an assay using HepaRG® spheroids can be used to determine the hepatotoxic potential or liability of drug candidates. See e.g., Walker et al., "The evolution of strategies to minimise the risk of human drug-induced liver injury (DILI) in drug discovery and development," (2020) *Archives of Toxicology*, Vol. 94: 2559-2585, which is hereby incorporated by reference herein in its entirety. Walker et al. have reported that results from HepaRG spheroid assays are correlated with drugs known to cause hepatotoxicity in humans with high sensitivity, specificity, and accuracy of 84%, 100%, and 89%, respectively, when a cut-off minimum effective concentration (MEC)<25×$C_{max.tot}$ is applied ($C_{max.tot}$ is the maximal total plasma concentration of drug, and MEC is the concentration that significantly crosses the vehicle control threshold of a cell health marker). In applying the HepaRG spheroid assay analysis to determining the hepatotoxic liability of ALDH-2 inhibitor compounds, consideration is made of the binding to plasma protein and the limitations to CNS penetration due to the blood-brain barrier. Thus, it is reasonable to assument a multiple of 100 in determining a most preferred ratio of MEC to $IC_{50}$ (ALDH-2) for ALDH-2 inhibitor compounds that exhibit low hepatotoxic liability. Accordingly, exemplary ratios of HepaRG spheroids assay MEC to the ALDH-2 inhibitor assay $IC_{50}$ indicating low hepatotoxic liability are most preferred to be >2500, followed by >250, and then >25 would be least preferred.

Pharmaceutical Compositions

In some embodiments of the methods of the present disclosure, it is contemplated that the ALDH-2 inhibitor is administered in the form of a pharmaceutical composition. The pharmaceutical composition comprising an ALDH-2 inhibitor includes a dosage comprising a therapeutically effective amount of the active ingredient, such as an ALDH-2 inhibitor compound of structural Formula (I) or Formula (II), or a pharmaceutically acceptable salt, ester, single stereoisomer, mixture of stereoisomers, or tautomer thereof, and one or more pharmaceutically acceptable excipients, carriers, including inert solid diluents and fillers, diluents, including sterile aqueous solution and various organic solvents, permeation enhancers, solubilizers and adjuvants.

As disclosed elsewhere herein, in some embodiments of the methods the step of administering can comprise administering a pharmaceutical composition, wherein the pharmaceutical composition contains an ALDH-2 inhibitor of structural Formula (I) or (II) (e.g., compounds (1a), (1b), and (1c)), or a pharmaceutically acceptable salt, ester, single stereoisomer, mixture of stereoisomers, or a tautomer of such a compound, and a pharmaceutically acceptable carrier. Accordingly, in some embodiments the present disclosure also provides a pharmaceutical composition, wherein the composition comprises a therapeutically effective amount of an ALDH-2 inhibitor and a pharmaceutically acceptable carrier.

In some embodiments, the pharmaceutical composition useful in the methods of the present disclosure is in a unit dosage form, such as a dosage form that contains the active ingredient (e.g., compound (1a)) in a single dosage form.

In some embodiments, the present disclosure provides a dosage form comprising a pharmaceutical composition of an ALDH-2 inhibitor (e.g., compound (1a)) and a pharmaceutically acceptable carrier, wherein the dosage form comprises ALDH-2 inhibitor in a therapeutically effective amount.

In some embodiments, the pharmaceutical composition comprises a dosage of an ALDH-2 inhibitor of Formula (I) in an amount of about 2.5 mg to about 1200 mg, about 5.0 mg to about 600 mg, about 15 mg to about 400 mg, or about 25 mg to about 200 mg. In some embodiments, the pharmaceutical composition comprises a dosage of an ALDH-2 inhibitor of Formula (I) in an amount of about 2.5 mg, about 5.0 mg, about 10 mg, about 15 mg, about 20 mg, about 25 mg, about 50 mg, about 100 mg, about 200 mg, about 300 mg, about 400 mg, about 500 mg, about 600 mg, about 800 mg, about 1000 mg, or about 1200 mg.

Such pharmaceutical compositions can be prepared using methods well known in the pharmaceutical art (see, e.g., *Remington's Pharmaceutical Sciences*, Mace Publishing Co., Philadelphia, PA 17th Ed. (1985) and *Modern Pharmaceutics*, Marcel Dekker, Inc. 3rd Ed. (G. S. Banker & C. T. Rhodes, Eds.). Methods of preparing pharmaceutical compositions of ALDH-2 inhibitor compounds are described in the present disclosure, including the Examples disclosed herein. Useful synthetic methods for ALDH-2 inhibitor compounds are also described in e.g., U.S. Pat. Nos. 7,951,813, 8,158,810, 8,673,966, 8,558,001, 8,575,353, 9,000,015, and 9,610,299, each of which is hereby incorporated by reference herein.

Modes of Administering ALDH-2 Inhibitors

In the uses and methods of the present disclosure it is contemplated that the pharmaceutical composition(s) comprising the ALDH-2 inhibitor compounds, such as a compound of Formula (I) or Formula (II) (e.g., compounds (1a), (1b), and (1c)), or a pharmaceutically acceptable salt, ester, single stereoisomer, mixture of stereoisomers, or a tautomer of such a compound, can be administered either as single or multiple doses, and by any of the accepted modes of administration of active ingredients having similar utility. For example, as described in U.S. Pat. No. 8,558,001, a pharmaceutical composition comprising an ALDH-2 inhibitor can be administered using a variety of different modes including rectal, buccal, intranasal, and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One exemplary route for administering that is useful in the methods of the present disclosure is oral. Oral administration may be via capsule, enteric coated tablets, or the like. Typically, in making the pharmaceutical compositions that include a medication containing an ALDH-2 inhibitor, such as compound of Formula (I) or Formula (II), the active ingredient(s) is diluted by an excipient and/or enclosed within a carrier in the form of a capsule, sachet, paper, or other container. When the excipient serves as a diluent, it can be a solid, semi-solid, or liquid material (as above), which acts as a vehicle, carrier or medium for the active ingredient. Thus, the pharmaceutical composition(s) suitable for administering in the methods of the disclosure can be in the dosage form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Suitable excipients for use in the pharmaceutical compositions comprising ALDH-2 inhibitors of the present disclosure are well known in the art and include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The pharmaceutical compositions can additionally include lubricating agents such as talc, magnesium stearate, and mineral oil; wetting agents; emulsifying and suspending agents; preserving agents such as methyl- and propylhydroxy-benzoates; sweetening agents; and flavoring agents.

Exemplary methods of preparing pharmaceutical compositions of ALDH-2 inhibitors suitable for use in the methods of the present disclosure are provided in the Examples.

The pharmaceutical compositions comprising ALDH-2 inhibitors useful in the methods of the present disclosure can be formulated so as to provide quick, sustained, or delayed release of the relevant active ingredient after administration by employing procedures known in the art. Controlled release drug delivery systems for oral administration include osmotic pump systems and dissolutional systems containing polymer-coated reservoirs or drug-polymer matrix formulations. Examples of controlled release systems are given in e.g., U.S. Pat. Nos. 3,845,770; 4,326,525; 4,902,514; and 5,616,345.

The pharmaceutical compositions comprising ALDH-2 inhibitors useful in the methods of the present disclosure can also be formulated for administration via transdermal delivery devices (e.g., "patches"). Such transdermal patches may be used to provide continuous or discontinuous infusion of the pharmaceutical compositions in controlled amounts. The construction and use of transdermal patches for the delivery of pharmaceutical compositions is well known in the art. See, e.g., U.S. Pat. Nos. 5,023,252, 4,992,445 and 5,001,139. Such patches may be constructed for continuous, pulsatile, or on demand delivery of the pharmaceutical composition(s). In some embodiments, the pharmaceutical composition(s) useful in the methods of the present disclosure are formulated in a unit dosage form.

Generally, ALDH-2 inhibitor compounds, such as the compounds of structural Formula (I) or (II) of the present disclosure, are known to be effective over a wide range of dosages and are administered as a pharmaceutical composition in a pharmaceutically effective amount. In some embodiments, for oral administration, each dosage unit contains from about 10 mg to 1 g of an ALDH-2 inhibitor compound Formula (I) or (II), or a pharmaceutically acceptable salt, ester, single stereoisomer, mixture of stereoisomers, or a tautomer of such a compound, in some embodiments from 25 mg to 1200 mg. In some embodiments, for parenteral administration, from 10 to 700 mg of an ALDH-2 inhibitor compound, such as compound of Formula (I) or Formula (II), or a pharmaceutically acceptable salt, ester, single stereoisomer, mixture of stereoisomers, or a tautomer of such a compound, or in some embodiments, from about 50 mg to 300 mg.

Generally, in the methods of the disclosure, the amount of the ALDH-2 inhibitor compound, such as compound of structural Formula (I) or (II), or a pharmaceutically acceptable salt, ester, single stereoisomer, mixture of stereoisomers, or a tautomer of such a compound, to be administered will be determined by a physician, in view of relevant circumstances of the subject being so treated, the chosen route of administration, and of course, the age, the weight, the severity of symptoms, the response of the individual subject to the treatment, and the like.

For preparing a solid pharmaceutical composition useful in the methods of the present disclosure, the active ingredient is mixed with a pharmaceutical excipient to form a solid preformulation composition containing a homogeneous mixture of the active ingredient and the excipients. When referring to these preformulation compositions as homogeneous, it is meant that the active ingredient is dispersed evenly throughout the composition so that the composition may be readily subdivided into equally effective unit dosage forms such as tablets, pills, and capsules. Tablets or pills may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Another exemplary mode for administering useful in the methods of the present disclosure is parenteral, particularly by injection. Pharmaceutical compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the active ingredients of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the known methods of preparation include vacuum-drying and freeze-drying techniques which yield a powder of the active ingredient plus any additional desired ingredient from a previously sterile-filtered solution thereof.

Pharmaceutical compositions that can be administered by inhalation or insufflation include solutions and suspensions in pharmaceutically acceptable, aqueous organic solvents, or mixtures thereof, and powders. The liquid or solid compositions may contain suitable pharmaceutically acceptable excipients as described herein and as known in the art. In some embodiments, the pharmaceutical composition of the ALDH-2 inhibitor compound of structural Formula (I) or (II) (e.g., compounds (1a), (1b), and (1c)), or a pharmaceutically acceptable salt, ester, single stereoisomer, mixture of stereoisomers, or a tautomer thereof, can be administered by the oral or nasal respiratory route for local or systemic effect. In some embodiments, the pharmaceutical compositions are prepared in pharmaceutically acceptable solvents which can be nebulized by use of inert gases. These nebulized solutions can be inhaled directly from the nebulizing device or the nebulizing device may be attached to a face mask tent, or intermittent positive pressure breathing machine. In some embodiments, the pharmaceutical compositions useful in the methods can be in solution, suspension, or powder compositions and can be administered, orally or nasally, from devices that deliver the formulation in an appropriate manner.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

The following Examples 1-10 describe methods for the synthesis of the exemplary ALDH-2 inhibitor compounds of structural Formulas (I) and (II) depicted in Table 1 (above).

Reagents used in the syntheses of Examples 1-10 were purchased from the commercial sources and were used as received. Other general methods and instrumentation used in the syntheses of Examples 1-10 were as follows. $^1$H NMR spectra were obtained on a Bruker AVANCE 300 spectrometer at 300 MHz and a Bruker AVANCE 400 spectrometer at 400 MHz with tetramethylsilane used as an internal reference. Thin-layer chromatography (TLC) was performed using Whatman No. 4500-101 (Diamond No. MK6F silica-gel 60 Å) plates. Mass spectra were obtained on a Waters Acquity UPLC-MS spectrometer using electro spray ionization, detector-SQD, column-Acquity BEH-C18, 1.7 g, 2.1× 50 mm, mobile phase-Acetonitrile: 10 mM Ammonium formate. HPLC analyses were performed on an Agilent 1200 series with PDA detector and Column Polaris C18-A, 100× 3.0 mm, and 2.6 μm. Chemical abbreviations used in the Examples are provided in Table 2 (above).

Example 1: Synthesis of 2-Chloro-6-methyl-N-((2-(3-oxopiperazin-1-yl)pyrimidin-5-yl)methyl)benzamide (1a)

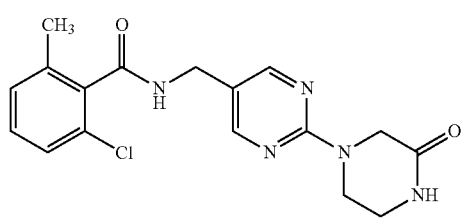 [SMILES: Cc1cccc(Cl)c1C(=O)NCc1cnc(N2CCNC(=O)C2)nc1]

Compound 1a was prepared via the synthesis summarized in Schemes 1 and 2 (below).

Scheme 1

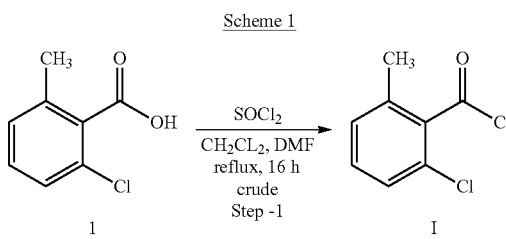

Scheme 2

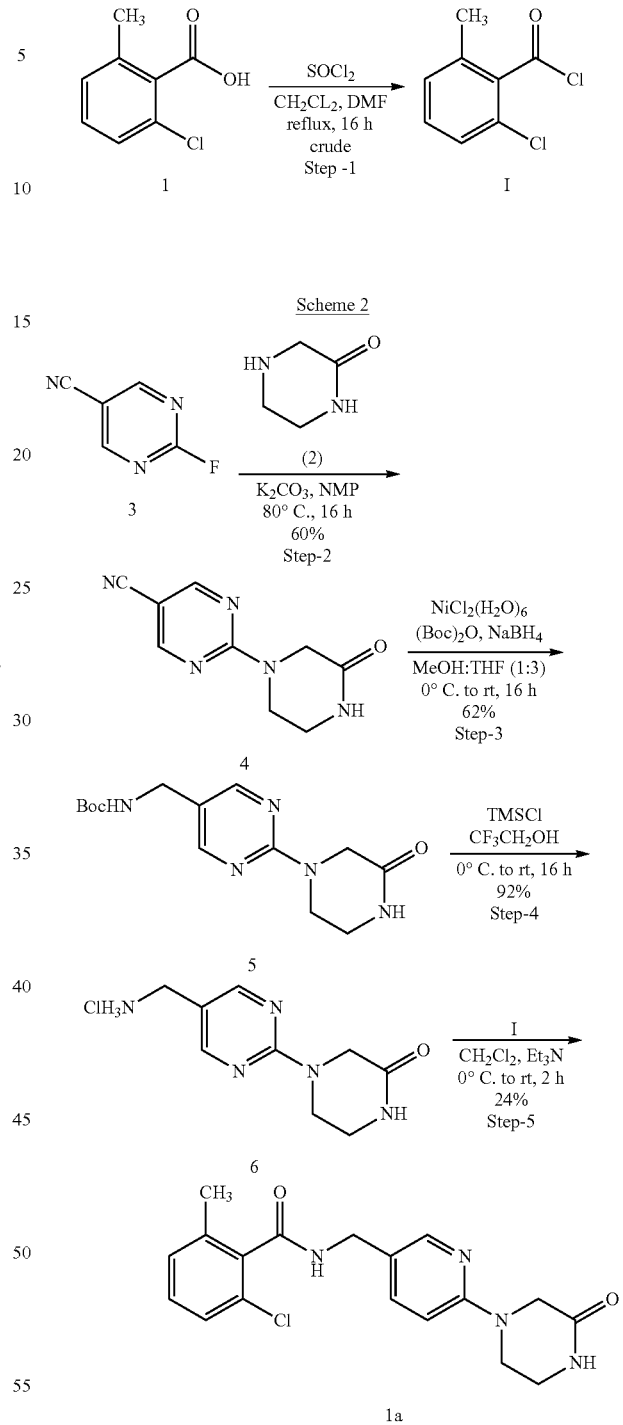

Step-1: Synthesis of 2-chloro-6-methylbenzoyl chloride (I): To a stirred solution of 4-chloro-2-methylbenzoic acid (1) (200 mg, 1.16 mmol) in anhydrous CH$_2$Cl$_2$ (5.0 mL) were added SOCl$_2$ (0.276 mL, 15.70 mmol) and DMF (0.05 mL) at 0° C. under N$_2$ atmosphere. The mixture was stirred to 55° C. for 16 h. The reaction mixture was concentrated under reduced pressure to afford crude 4-chloro-2-methylbenzoyl chloride (I) (200 mg) as a colourless liquid. The crude compound was directly used in Step-24.

Step-2: Synthesis of 2-(3-Oxopiperazin-1-yl)pyrimidine-5-carbonitrile (4): To a stirred solution of piperazin-2-one (2) (245 mg, 2.45 mmol) in NMP (1.8 mL K$_2$CO$_3$ (678 mg, 4.91 mmol) and 2-fluoropyrimidine-5-carbonitrile (3) (300 mg, 2.45 mmol) at room temperature under N$_2$ atmosphere. The reaction mixture was stirred at 80° C. for 1 h. The reaction mixture was poured into ice cold water (50 mL) and the precipitated solid was filtered and washed with water to afford 2-(3-oxopiperazin-1-yl)pyrimidine-5-carbonitrile (4) (260 mg, 60% yield) as an off white solid. $^1$H NMR (400 MHz, DMSO-d$_6$): δ 8.82 (s, 2H), 8.22 (s, 1H), 4.24 (s, 2H), 3.98 (t, J=5.2 Hz, 2H), 3.31-3.27 (m, 2H).

Step-3: Synthesis of tert-Butyl ((2-(3-oxopiperazin-1-yl)pyrimidin-5-yl)methyl)carbamate 55): To a stirred solution of 2-(3-oxopiperazin-1-yl)pyrimidine-5-carbonitrile (4) (9.00 g, 44.7 mmol) in MeOH:THF (1:3 ratio; 180 mL), were added NiCl$_2$·6H$_2$O (10.6 g, 44.7 mmol), (Boc)$_2$O (19.4 g, 89.4 mmol) and NaBH$_4$ (5.09 g, 134 mmol) at 0° C. under N$_2$ atmosphere. The reaction mixture was stirred at room temperature for 16 h. The residue was diluted with water and extracted with EtOAc (2×300 mL). The organic extract was separated, washed with water, brine (2×500 mL) and dried over Na$_2$SO$_4$. After evaporation of the solvent, the residue was purified by silica gel chromatography (5% of CH$_3$OH:CH$_2$Cl$_2$) to afford the tert-butyl ((2-(3-oxopiperazin-1-yl)pyrimidin-5-yl)methyl)carbamate (5) (230 mg, 62% yield) as an off white solid. $^1$H NMR (400 MHz, DMSO-d$_6$): δ 8.29 (s, 2H), 8.08 (brs, 1H) 7.31 (t, J=6.0 Hz, 1H), 4.14 (s, 2H), 3.95 (d, J=6.0 Hz, 2H), 3.87 (t, J=5.2 Hz, 2H), 3.25 (t, J=6.0 Hz, 2H), 1.37 (s, 9H). MS (ESI+APCI; multimode): 308.0 [M+H]$^+$.

Step-4: Synthesis of 4-(5-(Aminomethyl)pyrimidin-2-yl)piperazin-2-one hydrochloride (6): To a stirred solution of tert-butyl ((2-(3-oxopiperazin-1-yl)pyrimidin-5-yl)methyl)carbamate (5) (5.00 g, 16.3 mmol), in 2,2,2-trifluoroethanol (50.0 mL) was added TMSCl (5.93 mL, 49.3 mmol) at room temperature under N$_2$ atmosphere. The reaction mixture was stirred at room temperature for 3 h. The solvent was removed under reduced pressure and MTBE added. The solids were filtered and washed with MTBE to afford 4-(5-(aminomethyl)pyrimidin-2-yl)piperazin-2-one hydrochloride (6) (330 mg, 92% yield) as an off white solid. $^1$H NMR (400 MHz, DMSO-d$_6$): δ 8.54 (s, 2H), 8.44 (m, 2H), 8.13 (s, 1H), 4.18 (s, 2H), 3.92-3.83 (m, 4H), 3.29-3.26 (m, 2H).

Step-5: Synthesis of 2-Chloro-6-methyl-N-((2-(3-oxopiperazin-1-yl)pyrimidin-5-yl)methyl)benzamide (1a): To a stirred solution of 4-(5-(aminomethyl)pyrimidin-2-yl)piperazin-2-one hydrochloride (6) (150 mg, 0.956 mmol) in CH$_2$Cl$_2$ (5.0 mL), were added Et$_3$N (0.22 mL, 1.66 mmol) and 4-chloro-2-methylbenzoyl chloride (I) (130 mg, 0.58 mmol) at 0° C. under N$_2$ atmosphere. The reaction mixture was stirred at room temperature for 1 h. The reaction mixture was diluted with water, basified with saturated aqueous sodium bicarbonate, and extracted with 10% CH$_3$OH in CH$_2$Cl$_2$ (2×100 mL). The organic layer was separated and washed with water and brine (2×50 mL) and dried over Na$_2$SO$_4$. The solvent was removed under reduced pressure. The residue was purified by silica gel chromatography (5% of CH$_3$OH:CH$_2$Cl$_2$) to afford the 2-chloro-6-methyl-N-((2-(3-oxopiperazin-1-yl)pyrimidin-5-yl)methyl)benzamide (1a) (56.0 mg, 24% yield) as an off white solid. $^1$H NMR (400 MHz, DMSO-d$_6$): δ 8.92 (t, J=6.0 Hz, 1H), 8.41 (s, 2H), 8.06 (d, J=7.6 Hz, 1H), 7.29-7.19 (m, 3H), 4.29 (d, J=5.6 Hz, 2H), 4.15 (s, 2H), 3.89 (t, J=5.6 Hz, 2H) 3.28-3.24 (m, 2H), 2.19 (s, 3H). MS (ESI+APCI; multimode): 360.0 [M+H]$^+$. HPLC: 99.9 (% of AUC).

Example 2: Synthesis of 2-Chloro-N-((2-(3-oxopiperazin-1-yl)pyrimidin-5-yl)methyl)benzamide (1b)

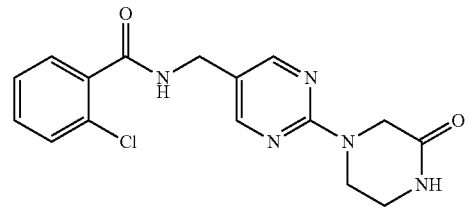

Compound 1b was prepared via the synthesis summarized in Schemes 3 and 4 (below).

Scheme 3

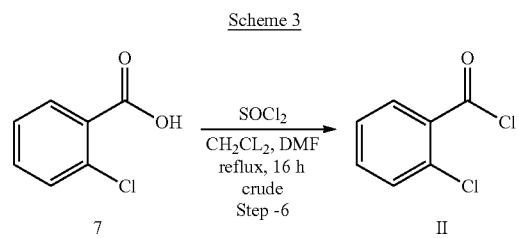

Scheme 4

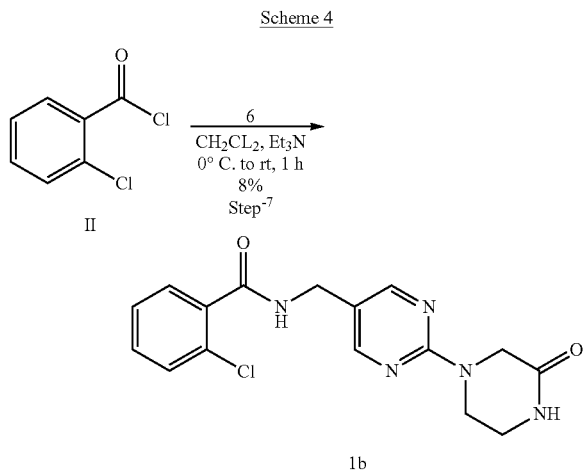

Step-6: Synthesis of 2-chlorobenzoyl chloride (II): To a stirred solution of 2-chlorobenzoic acid (7) (200 mg, 1.16 mmol) in anhydrous CH$_2$Cl$_2$ (5.0 mL) were added SOCl$_2$ (0.276 mL, 15.70 mmol) and DMF (0.05 mL) at 0° C. under N$_2$ atmosphere. The mixture was stirred to 55° C. for 16 h. The reaction mixture was concentrated under reduced pressure to afford crude 2-chlorobenzoyl chloride (II) (200 mg) as a colourless liquid. The crude compound was directly used in Step-25.

Step-25: Synthesis of 2-Chloro-N-((2-(3-oxopiperazin-1-yl)pyrimidin-5-yl)methyl)benzamide (1b): To a stirred solution 4-(5-(aminomethyl)pyrimidin-2-yl)piperazin-2-one hydrochloride (6) (150 mg, 0.956 mmol) (prepared as in Example 1) in CH$_2$Cl$_2$ (5.0 mL), were added Et$_3$N (0.22 mL, 1.66 mmol) and 2-chlorobenzoyl chloride (II) (130 mg, 0.58 mmol) at 0° C. under N$_2$ atmosphere. The reaction mixture was stirred at room temperature for 1 h. The reaction mixture was diluted with water, basified with saturated aqueous sodium bicarbonate, and extracted with 10% CH$_3$OH in CH$_2$Cl$_2$ (2×100 mL). The organic layer was separated and washed with water and brine (2×50 mL) and dried over Na$_2$SO$_4$. The solvent was removed under reduced pressure. The residue was purified by silica gel chromatography (5% of CH$_3$OH in CH$_2$Cl$_2$) to afford the 2-chloro-N-((2-(3-oxopiperazin-1-yl)pyrimidin-5-yl)methyl)benzamide (1b) (15.0 mg, 8% yield) as an off white solid. $^1$H NMR (400 MHz, DMSO-d$_6$): δ 8.89 (t, J=5.6 Hz, 1H), 8.40 (s, 2H), 8.07 (brs, 1H), 7.50-7.36 (m, 4H), 4.28 (d, J=5.6 Hz, 2H), 4.15 (s, 2H), 3.90 (t, J=5.2 Hz, 2H), 3.25 (t, J=4.0 Hz, 2H). MS (ESI+APCI; multimode): 346.0 [M+H]$^+$. HPLC: 98.5 (% of AUC).

Example 3: Synthesis of 4-Chloro-2-methyl-N-((2-(3-oxopiperazin-1-yl)pyrimidin-5-yl)methyl)nicotinamide (1c)

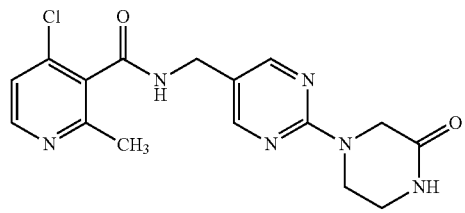

1c

Compound 1c was prepared via the synthesis summarized in Scheme 5 (below).

Scheme 5

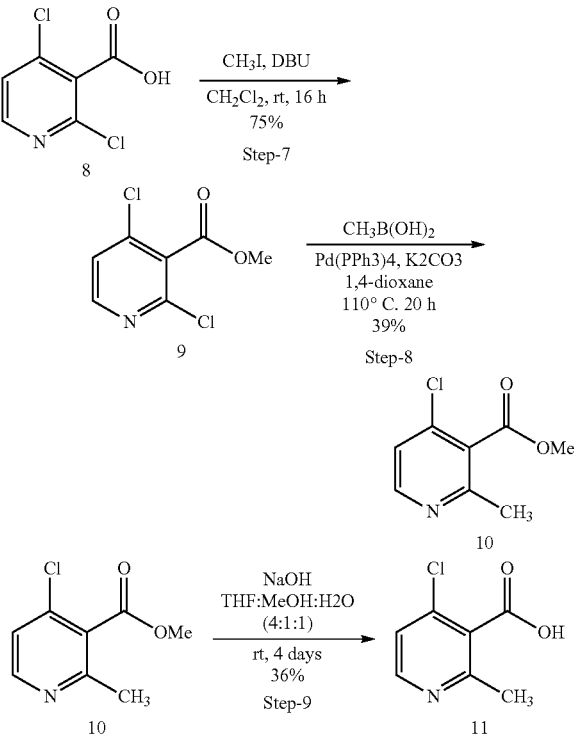

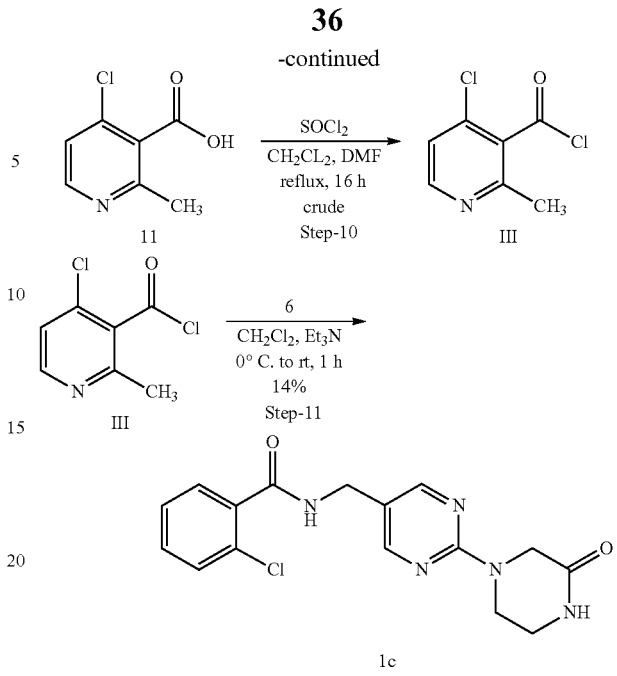

Step-7: Synthesis of methyl 2,4-dichloronicotinate (9): To a stirred solution of 2,4-dichloronicotinic acid (8) (5.00 g, 26.04 mmol) in CH$_3$CN (50.0 mL), were added DBU (7.76 mL, 52.08 mmol) and CH$_3$I (2.30 mL, 39.06 mmol) at 0° C. under N$_2$ atmosphere. The reaction mixture was stirred at room temperature for 16 h. The solvent was removed under reduced pressure. The residue was diluted with water and extracted with EtOAc (2×500 mL). The organic extract was separated, washed with water, brine (2×500 mL) and dried over Na$_2$SO$_4$. After evaporation of the solvent, the residue was purified by silica-gel chromatography (5% EtOAc in hexanes) to afford methyl 2, 4-dichloronicotinate (9) (4.00 g, 75% yield) as a pale-yellow solid. $^1$H NMR (400 MHz, CDCl$_3$): δ 8.35 (d, J=5.6 Hz, 1H), 7.34 (d, J=5.2 Hz, 1H), 4.01 (s, 3H).

Step-8: Synthesis of methyl 4-chloro-2-methylnicotinate (10): To a stirred solution of methyl 2,4-dichloronicotinate (9) (2.00 g, 9.705 mmol) in 1,4-dioxane (20.0 mL), were added methylboronic acid (1.16 g, 19.40 mmol) and K$_2$CO$_3$ (4.02 g, 29.12 mmol). The mixture was de-gassed with Ar (g) for 10 min. Pd(PPh$_3$)$_4$ (561 mg, 0.48 mmol) was added in one lot to the reaction mixture under N$_2$ atmosphere. The reaction mixture was stirred at 110° C. for 20 h. The reaction mixture was diluted with water and extracted with EtOAc (2×100 mL). The organic extract was separated, washed with water, brine (2×50 mL) and dried over Na$_2$SO$_4$. After evaporation of the solvent, the residue was purified by silica-gel chromatography (5% EtOAc in hexanes) to afford methyl 4-chloro-2-methylnicotinate (3) (700 mg, 39% yield) as a pale-yellow solid. $^1$H NMR (400 MHz, CDCl$_3$): δ 8.43 (d, J=5.6 Hz, 1H), 7.21 (d, J=5.2 Hz, 1H), 3.98 (s, 3H), 2.57 (s, 3H). MS (ESI+APCI; multimode): 186.0 [M+H]$^+$.

Step-9: Synthesis of 4-chloro-2-methylnicotinic acid (11): To a stirred solution of methyl 4-chloro-2-methylnicotinate (10) (700 mg, 3.78 mmol) in THF:MeOH:H$_2$O (4:1:1 ratio; 20.0 mL), was added aqueous NaOH (6.25 M; 1.12 mL) at room temperature. The reaction mixture was stirred at room temperature for 4 days. The reaction mixture was added 2N aqueous HCl to pH 7. The reaction mixture was extracted with EtOAc (2×50 mL). The aqueous layer was concentrated under reduced pressure to minimum amount of solvent and purified by reverse phase C-18 column chromatography (50% of CAN in $H_2O$) to afford 4-chloro-2-methylnicotinic acid (11) (250 mg, 36% yield) as an off white solid. $^1H$ NMR (400 MHz, DMSO-$d_6$): δ 14.10 (brs, 1H), 8.46 (d, J=5.2 Hz, 1H), 7.48 (dd, J=0.4 Hz, 5.6 Hz, 1H), 2.50 (s, 3H). MS (ESI+APCI; multimode): 172.0 $[M+H]^+$.

Step-10: Synthesis of 4-Chloro-2-methylnicotinoyl chloride (III): To a stirred solution of 4-chloro-2-methylnicotinic acid (11) (200 mg, 1.16 mmol) in anhydrous $CH_2Cl_2$ (5.0 mL) were added $SOCl_2$ (0.276 mL, 15.70 mmol) and DMF (0.05 mL) at 0° C. under $N_2$ atmosphere. The mixture was stirred to 55° C. for 16 h. The reaction mixture was concentrated under reduced pressure to afford crude 4-chloro-2-methylnicotinoyl chloride (III) (200 mg) as a colourless liquid. The crude compound was directly used in step-26.

Step-11: Synthesis of 4-Chloro-2-methyl-N-((2-(3-oxopiperazin-1-yl)pyrimidin-5-yl)methyl)nicotinamide (10): To a stirred solution 4-(5-(aminomethyl)pyrimidin-2-yl)piperazin-2-one hydrochloride (20) (150 mg, 0.956 mmol) (prepared as in Example 1) in $CH_2Cl_2$ (5.0 mL), were added $Et_3N$ (0.22 mL, 1.66 mmol) and 4-chloro-2-methylnicotinoyl chloride (III) (130 mg, 0.58 mmol) at 0° C. under $N_2$ atmosphere. The reaction mixture was stirred at room temperature for 1 h. The reaction mixture was diluted with water, basified with saturated aqueous sodium bicarbonate, and extracted with 10% $CH_3OH$ in $CH_2Cl_2$ (2×100 mL). The organic layer was separated and washed with water and brine (2×50 mL) and dried over $Na_2SO_4$. The solvent was removed under reduced pressure. The residue was purified by was purified by C-18 column chromatography using 50% of ACN:$H_2O$ to afford the 4-chloro-2-methyl-N-((2-(3-oxopiperazin-1-yl)pyrimidin-5-yl)methyl)nicotinamide (1c) (20.0 mg, 14% yield) as an off white solid. $^1H$ NMR (400 MHz, DMSO-$d_6$): δ 9.11 (t, J=5.6 Hz, 1H), 8.42-8.41 (m, 3H), 8.09 (brs, 1H), 7.43 (d, J=5.6 Hz, 1H), 4.32 (d, J=6.0 Hz, 2H), 4.16 (s, 2H), 3.89 (t, J=5.2 Hz, 2H), 3.27 (t, J=3.6 Hz, 2H), 2.38 (s, 3H). MS (ESI+APCI; multimode): 361.0 $[M+H]^+$. HPLC: 99.3 (% of AUC).

Example 4: ALDH-1, ALDH-2, ALDH-3, MAO-A, MAO-B and HepaRG Spheroid Assays of ALDH-2 Inhibitor Compounds This example illustrates studies of the exemplary ALDH-2 inhibitor compounds of the present disclosure in assays measuring inhibition of ALDH-2, ALDH-1, ALDH-3, as well as MAO-A, and MAO-B. The example also illustrates studies of the compounds in HepaRG 3D spheroid assay that provides a measure of potential hepatotoxic liability.

Materials and Methods

A. ALDH-2 inhibition assay: The ALDH-2 reaction mixture used in the assay contained 125 µM formaldehyde, 75 µM NAD+, 20 mM NaCl, 10 mM $MgCl_2$, and 20 nM recombinant human ALDH-2 in 50 mM Hepes buffer, pH 7.5 in a final volume of 10 µL using 384-well Corning 3820 plates. After 60 min of pre-incubation of the test ALDH-2 inhibitor compound with ALDH-2, the reaction was started by adding NAD+ and formaldehyde and the assay reaction mixture was allowed to proceed for 60 minutes. Activity of the ALDH-2 enzyme was determined by monitoring NADH formation using Perkin-Elmer Envision Reader with excitation and emission wavelengths set at 340 and 460 nm, respectively. Inhibition was determined as $IC_{50}$, which refers to the concentration of the test ALDH-2 inhibitor compound that inhibited the reaction by 50%.

B. ALDH-1 inhibition assay: The ALDH-1 reaction mixture used in the assay contained 100 µM formaldehyde, 2.5 mM NAD+, 20 mM NaCl, 10 mM $MgCl_2$, 1 mM dithiothreitol (DTT; reducing agent), and 50 nM recombinant human ALDH-1 in 50 mM Hepes buffer, pH 7.5 in a final volume of 10 µL using 384-well Corning 3820 plates. After 60 min of pre-incubation of the test ALDH-2 inhibitor compound with ALDH-1, the reaction was started by adding NAD+ and formaldehyde and the assay reaction mixture was allowed to proceed for 60 minutes. Activity of the ALDH-1 enzyme was determined by monitoring NADH formation using Perkin-Elmer Envision Reader with excitation and emission wavelengths set at 340 and 460 nm, respectively. Inhibition was determined as $IC_{50}$, which refers to the concentration of the test ALDH-2 inhibitor compound that inhibited the reaction by 50%.

C. ALDH-3 inhibition assay: The ALDH-3 reaction mixture used in the assay contained 200 µM benzaldehyde, 2.5 mM NAD+, 20 mM NaCl, 10 mM $MgCl_2$, and 10 nM recombinant human ALDH-3 in 50 mM Hepes buffer, pH 7.5 in a final volume of 10 µL using 384-well Corning 3820 plates. After 60 min of pre-incubation of the test ALDH-2 inhibitor compound with ALDH-3, the reaction was started by adding NAD+ and benzaldehyde and the assay reaction mixture was allowed to proceed for 60 minutes. Activity of the ALDH-3 enzyme was determined by monitoring NADH formation using Perkin-Elmer Envision Reader with excitation and emission wavelengths set at 340 and 460 nm, respectively. Inhibition was determined as $IC_{50}$, which refers to the concentration of the test ALDH-2 inhibitor compound that inhibited the reaction by 50%.

D. MAO-A and MAO-B inhibition assays: MAO assays included luminogenic MAO substrate, reaction buffers, Luciferin Detection, and a reconstitution buffer with esterase. The MAO reaction mixture used in the assay included microsome contained MAO-A (2 µg) or MAO-B (10 µg), 160 µM substrate for MAO-A or 16 µM substrate for MAO-B, MAO-A buffer (100 mM Hepes buffer, pH 7.5, 5% glycerol) or MAO-B buffer (100 mM Hepes, pH 7.5, 5% glycerol, 10% dimethyl sulfoxide) in a final volume of 30 µL. After 20 minutes of pre-incubation of the MAO-A or MAO-B enzyme with the test ALDH-2 inhibitor compound, the reaction was initiated by adding enzyme substrate and the 60 reaction was allowed to proceed for 60 minutes. Reconstituted Luciferin Detection Reagent (30 µL) was then added is added to simultaneously stop the MAO reaction and convert the methyl ester derivative to luciferin and produce light. The amount of light produced is directly proportional to the activity of MAO. The mixtures were further incubated for 20 minutes and activity of the enzyme was determined using Perkin-Elmer Envision Reader. Inhibition was determined as $IC_{50}$, which refers to the concentration of the test ALDH-2 inhibitor compound that inhibited the reaction by 50%.

E. HepaRG® 3D spheroid assay: The HepaRG 3D spheroid assay is described in Walker et al., "The evolution of strategies to minimise the risk of human drug-induced liver injury (DILI) in drug discovery and development," (2020) *Archives of Toxicology*, Vol. 94: 2559-2585. Briefly, HepaRG® cells were seeded into ultra-low adhesion 96-well black walled clear bottomed spheroid microplates. Following formation, the spheroids were dosed with test ALDH-2 inhibitor compound at a range of concentrations to yield an 8 point dose response curve with top concentration at 100 mM (3 replicates per concentration) at days 1, 4, 7 and 10 and 13. At the end of the incubation period, the spheroids were loaded with the relevant dye/antibody for each cell health marker (spheroid count, spheroid size, DNA structure, mitochondrial mass, mitochondrial membrane potential, oxidative stress, glutathione content, and cellular ATP). The plates were then scanned using an automated fluorescent cellular imager, ArrayScan® (Thermo Scientific Cellomics). The minimum effective concentration ("MEC") was determined as the amount of the tested compound that significantly crosses vehicle control threshold of cell health marker.

Results

The results of the ALDH-2, ALDH-1, ALDH-3, MAO-A, MAO-B, and HepaRG 3D spheroid assays for the exemplary ALDH-2 inhibitor compounds of Table 1 are summarized in Table 3 below.

TABLE 3

| Compound | Enzymatic Assays* $IC_{50}$ (µM) | | | | | HepaRG 3D Spheroid** MEC (µM) | Ratio MEC to ALDH-2 |
| --- | --- | --- | --- | --- | --- | --- | --- |
| | ALDH2 | ALDH-1 | ALDH-3 | MAO-A | MAO-B | | |
| (1a) | 0.089 | >10 | >10 | >10 | >10 | No Effect | >1128 |
| (1b) | 0.264 | >10 | >10 | >10 | >10 | No Effect | >378 |
| (1c) | 0.088 | >10 | >10 | >10 | >10 | No Effect | >1136 |

*10 µM = highest concentration tested
**100 µM = highest concentration tested

Example 5: Formulation of Pharmaceutical Compositions

This example illustrates formulations of the pharmaceutical compositions comprising ALDH-2 inhibitors of structural Formula (I) and Formula (II) that can be used in the methods of the present disclosure for treating addiction to a substance or condition of addiction or abuse.

Hard gelatin capsules: The ingredients listed below are mixed and filled into hard gelatin capsules:

| Ingredient | Quantity (mg/capsule) |
| --- | --- |
| Active Ingredient | 30.0 |
| Starch | 305.0 |
| Magnesium stearate | 5.0 |

240 mg Tablets: The ingredients listed below are blended and compressed to form 240 mg tablets:

| Ingredient | Quantity mg/tablet |
| --- | --- |
| Active Ingredient | 25.0 |
| Cellulose, microcrystalline | 200.0 |
| Colloidal silicon dioxide | 10.0 |
| Stearic acid | 5.0 |

120 mg Tablets: The ingredients listed below are blended and compressed as described below to form 120 mg tablets:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Suppositories: Suppositories each containing 25 mg of active ingredient, are made as follows:

| Ingredient | Quantity |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Suspensions: A suspension containing 50 mg of active ingredient per 5.0 mL dose, is made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Subcutaneous: a subcutaneous formulation is prepared as follows:

| Ingredient | Quantity |
| --- | --- |
| Active Ingredient | 5.0 mg |
| Corn Oil | 1.0 mL |

Injectable: an injectable formulation is prepared by combining the following ingredients:

| Ingredient | Quantity |
| --- | --- |
| Active ingredient | 2.0 mg/mL |
| Mannitol, USP | 50 mg/mL |
| Gluconic acid, USP | q.s. (pH 5-6) |
| Water (distilled, sterile) | q.s. to 1.0 mL |
| Nitrogen Gas, NF | q.s. |

Topical: a topical preparation is prepared by combining the following ingredients as described below:

| Ingredients | Quantity (g) |
| --- | --- |
| Active ingredient | 0.01-1 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the inventions.

What is claimed is:

1. A compound of structural Formula (I):

Formula (I)

wherein:
$X^1$ is N or $CR^3$, $X^2$ is N or $CR^4$, $X^3$ is N or $CR^6$, with the proviso that no more than one of $X^1$, $X^2$, and $X^3$ is N;
$R^{10}$ is H, optionally substituted $C_{1-6}$ alkyl, —$CH_2OH$, —$CH_2OP(O)(OR^{20})(OR^{21})$;
$R^{11}$ is H, halogen, optionally substituted $C_{1-6}$ alkyl, or cycloalkyl;
$R^7$ is H, or optionally substituted $C_{1-6}$ alkyl;
each of $R^2$, $R^3$, $R^4$, $R^5$, $R^6$, $R^8$, and $R^9$ is independently H, halogen, —$CF_3$, —OH, —$CH_2OH$, —CN, optionally substituted alkyl, optionally substituted alkylene, optionally substituted alkynyl, optionally substituted alkoxy, optionally substituted cycloalkyl, optionally substituted aryl, optionally substituted aralkyl, optionally substituted heteroaryl, optionally substituted heteroaralkyl, optionally substituted heterocyclyl, aminocarbonyl, acyl, acylamino, —O—($C_1$ to $C_6$-alkyl)-O—($C_1$ to $C_6$-alkyl), —$CH_2OP(O)(OR^{20})(OR^{21})$, —$SO_2NR^{24}R^{25}$; or —$NR^{24}R^{25}$, with the proviso that $R^2$ and $R^6$ are not both Cl when $X^1$ is $CR^3$, $X^2$ is $CR^4$, and $X^3$ is $CR^6$;
each of $R^{20}$ and $R^{21}$ is independently $Na^+$, $Li^+$, $K^+$, hydrogen, $C_{1-6}$ alkyl; or $R^{20}$ and $R^{21}$ can be combined to represent a single divalent cation $Zn^{2+}$, $Ca^{2+}$, or $Mg^{2+}$; and
each of $R^{24}$ and $R^{25}$ is independently chosen from hydrogen or $C_{1-6}$ alkyl or when combined together with the nitrogen to which they are attached form a heterocycle;
or a pharmaceutically acceptable salt, ester, single stereoisomer, mixture of stereoisomers, or a tautomer thereof.

2. The compound of claim 1, wherein each of $R^7$, $R^8$, $R^9$, $R^{10}$, and $R^{11}$ are H.

3. The compound of claim 1, wherein $X^1$ is $CR^3$, $X^2$ is $CR^4$, and $R^3$, $R^4$, and $R^5$ are independently H, Cl, F, $CH_3$, or $CF_3$; optionally, wherein each of $R^3$, $R^4$, and $R^5$ are H.

4. The compound of claim 1, wherein:
(a) $R^2$ is selected from H, Cl, F, or $CH_3$; and/or
(b) $R^6$ is selected from H, Cl, F, or $CF_3$.

5. The compound of claim 1, wherein the compound is selected from compounds (1a), (1b), and (1c)

(1a)

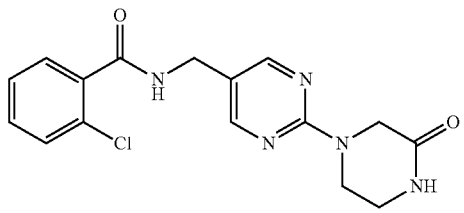 [SMILES: O=C1CN(c2ncc(CNC(=O)c3ccccc3Cl)cn2)CCN1] (1b)

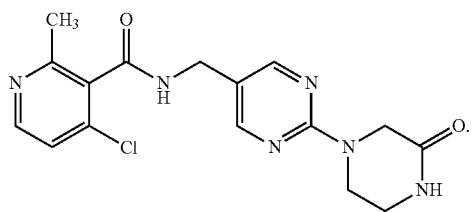 [SMILES: Cc1nccc(Cl)c1C(=O)NCc1cnc(N2CCNC(=O)C2)nc1] (1c)

6. A pharmaceutical composition comprising a therapeutically effective amount of the compound of claim 1 and a pharmaceutically acceptable carrier.

7. A method of treating chemical dependency on a substance or condition of addiction comprising administering a pharmaceutical composition of claim 6.

8. The method of claim 7, wherein the substance or condition of addiction is selected from the group consisting of alcohol, nicotine, cocaine, opiates, amphetamines, compulsive eating disorder, and/or anxiety disorder.

9. A method of treating compulsive eating disorder comprising administering to a human patient a pharmaceutical composition of claim 6.

10. A method of treating anxiety disorder comprising administering to a human patient a pharmaceutical composition of claim 6.

* * * * *